US012653615B2

(12) United States Patent
Weiss et al.

(10) Patent No.: US 12,653,615 B2
(45) Date of Patent: Jun. 16, 2026

(54) METHOD, DEVICE, AND SYSTEM FOR IMAGE GENERATION BASED ON CALCULATED ROBOTIC ARM POSITIONS

(71) Applicant: Mazor Robotics Ltd., Caesarea (IL)

(72) Inventors: Noam Weiss, Haifa (IL); Yizhaq Shmayahu, Ramat HaSharon (IL)

(73) Assignee: Mazor Robotics Ltd., Caesarea (IL)

( * ) Notice: Subject to any disclaimer, the term of this patent is extended or adjusted under 35 U.S.C. 154(b) by 777 days.

(21) Appl. No.: 17/375,834

(22) Filed: Jul. 14, 2021

(65) Prior Publication Data

US 2022/0104878 A1 Apr. 7, 2022

Related U.S. Application Data

(60) Provisional application No. 63/088,372, filed on Oct. 6, 2020.

(51) Int. Cl.
A61B 34/10 (2016.01)
A61B 8/00 (2006.01)
(Continued)

(52) U.S. Cl.
CPC ............ *A61B 34/10* (2016.02); *A61B 8/4218* (2013.01); *A61B 8/483* (2013.01); *A61B 8/485* (2013.01);
(Continued)

(58) Field of Classification Search
CPC ....... A61B 34/10; A61B 34/30; A61B 8/4218; A61B 8/483; A61B 8/485;
(Continued)

(56) References Cited

U.S. PATENT DOCUMENTS 7,859,400 B2 12/2010 Urbaszek et al.
8,364,245 B2 1/2013 Kruecker
(Continued)

FOREIGN PATENT DOCUMENTS

CN 108601669 9/2018
CN 110494096 11/2019
(Continued)

OTHER PUBLICATIONS

International Preliminary Report on Patentability for International (PCT) Patent Application No. PCT/IB2021/056405, dated Apr. 20, 2023 9 pages.
(Continued)

*Primary Examiner* — Jason Holloway
*Assistant Examiner* — Christopher A Buksa
(74) *Attorney, Agent, or Firm* — Sheridan Ross P.C.

(57) ABSTRACT

A method, device, and system for obtaining time of flight images is provided. A surgical plan may be received and a first path for a first robotic arm and a second path for a second robotic arm may be determined based on the surgical plan. The first robotic arm may be caused to move on the first path and may be configured to hold a transducer. The second robotic arm may be caused to move on the second path and may be configured to hold a receiver. At least one image may be received from the receiver, the image depicting patient anatomy and generated using time-of-flight measurements.

18 Claims, 8 Drawing Sheets

(51) Int. Cl.

| | |
|---|---|
| *A61B 34/30* | (2016.01) |
| *B25J 9/00* | (2006.01) |
| *B25J 9/16* | (2006.01) |
| *G01S 17/894* | (2020.01) |
| *G16H 20/40* | (2018.01) |
| *G16H 30/20* | (2018.01) |
| *G16H 40/63* | (2018.01) |

(52) U.S. Cl.
CPC ............. *A61B 34/30* (2016.02); *B25J 9/0087* (2013.01); *B25J 9/1664* (2013.01); *G01S 17/894* (2020.01); *G16H 20/40* (2018.01); *G16H 30/20* (2018.01); *G16H 40/63* (2018.01); *A61B 2034/105* (2016.02); *G05B 2219/39083* (2013.01); *G05B 2219/45117* (2013.01)

(58) Field of Classification Search
CPC .. A61B 2034/105; G16H 20/40; G16H 30/20; G16H 40/63; G01S 17/894; B25J 9/0087; B25J 9/1664; G05B 2219/45117
See application file for complete search history.

(56)                References Cited

U.S. PATENT DOCUMENTS

| | | | |
|---|---|---|---|
| 9,320,916 B2 | 4/2016 | Sumanaweera et al. | |
| 9,592,096 B2 | 3/2017 | Maillet et al. | |
| 9,833,292 B2 | 12/2017 | Kostrzewski et al. | |
| 10,417,357 B2 | 9/2019 | Franklin et al. | |
| 2015/0297177 A1* | 10/2015 | Boctor ................... | A61B 34/30 901/47 |
| 2015/0305828 A1 | 10/2015 | Park et al. | |
| 2016/0030117 A1 | 2/2016 | Mewes | |
| 2017/0333138 A1 | 11/2017 | Arata et al. | |
| 2019/0021795 A1 | 1/2019 | Crawford et al. | |
| 2019/0069957 A1 | 3/2019 | Barral et al. | |
| 2020/0015923 A1 | 1/2020 | Scheib et al. | |
| 2020/0297358 A1* | 9/2020 | Cameron ............... | A61B 90/11 |
| 2021/0196384 A1* | 7/2021 | Shelton, IV ........... | A61B 34/10 |

FOREIGN PATENT DOCUMENTS

| | | | |
|---|---|---|---|
| EP | 2554137 | 2/2013 | |
| EP | 3096703 | 3/2018 | |
| EP | 3306567 | 4/2018 | |
| WO | WO-2012065058 A2 * | 5/2012 | ............ A61B 34/30 |
| WO | WO 2017/214428 | 12/2017 | |

OTHER PUBLICATIONS

Aalamifar et al. "Image reconstruction for robot assisted ultrasound tomography," Progress in Biomedical Optics and Imaging, SPIE—International Society for Optical Engineering, Apr. 2016, vol. 9790, Article 979017, 11 pages.

International Search Report and Written Opinion for International (PCT) Patent Application No. PCT/IB2021/056405, dated Nov. 4, 2021 12 pages.

"Spine Navigation," 7D Surgical, Mar. 27, 2020, 7 pages.

Amin et al. "Ultrasound Registration of the Bone Surface for Surgical Navigation," Computer Aided Surgery, 2003, vol. 8, pp. 1-16.

Official Action with English Translation for China Patent Application No. 202180068366.0, dated Feb. 4, 2026, 22 pages.

\* cited by examiner

200

202 — Receive a 3D model

204 — Calculate one or more poses

206 — Receive an image from an imaging device at each of the one or more poses to yield an image set 208 — Update the 3D model based on at least one image from the image set and the pose corresponding to the at least one image

300

302  Calculate a second set of poses for the imaging device

304  Receive an updated image from the imaging device at each pose of the second set of poses to yield an updated image set 306  Update the updated 3D model using at least one updated image and based on the pose corresponding to the at least one updated image

400

402 — Receive a first image of an anatomical portion of a patient

404 — Calculate one or more poses

406 — Receive a second image from an imaging device at each of the one or more poses 408 — Align, based at least in part on the one or more poses, an anatomical element in each second image with a corresponding anatomical element in the first image 410 — Register an image space to a patient space based on the alignment

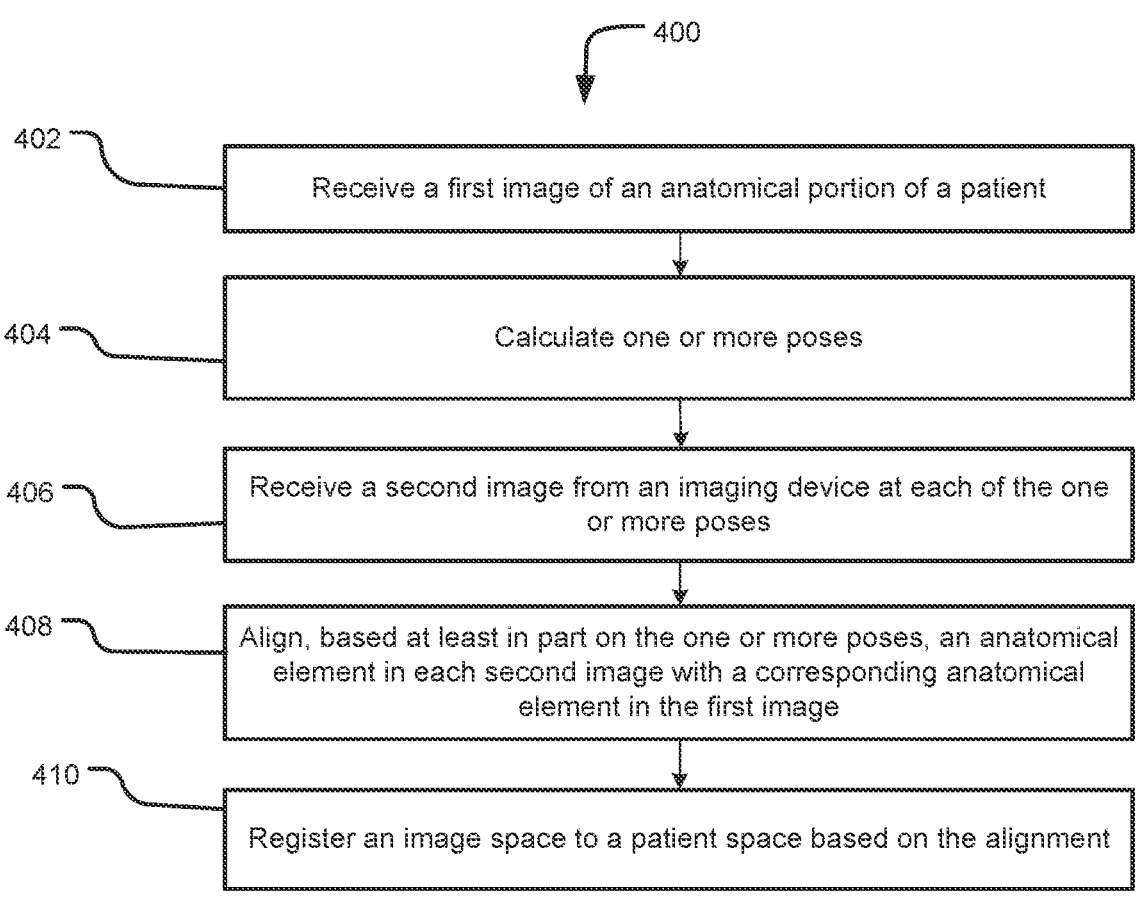

FIG. 4

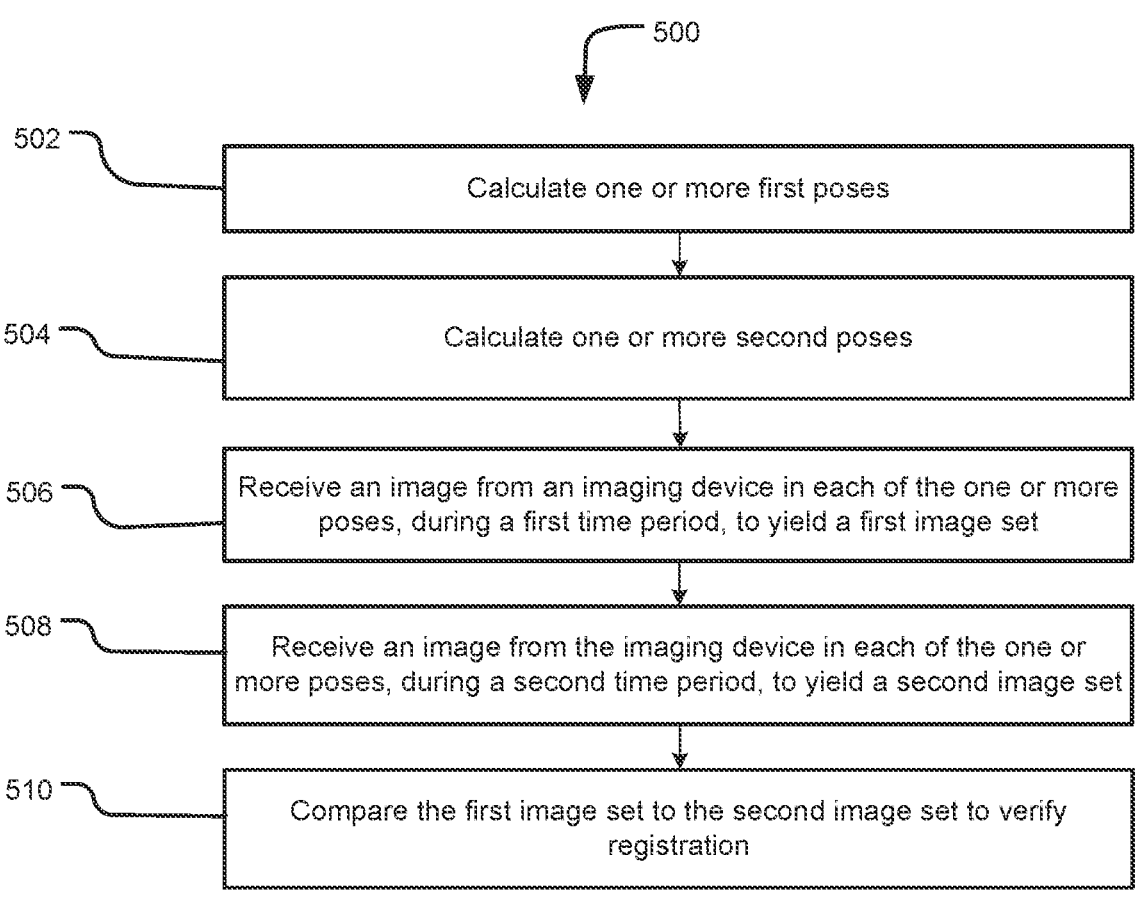

502 — Calculate one or more first poses

504 — Calculate one or more second poses

506 — Receive an image from an imaging device in each of the one or more poses, during a first time period, to yield a first image set 508 — Receive an image from the imaging device in each of the one or more poses, during a second time period, to yield a second image set 510 — Compare the first image set to the second image set to verify registration

602 — Receive a surgical plan

604 — Identify image information for the surgical plan

606 — Determine a pose for the identified imaging device

608 — Determine at least one setting of the identified imaging device based on the pose and the plan 610 — Receive an image from the identified imaging device at the determined pose using the determined at least one setting

800

802 — Receive a surgical plan

804 — Determine a first path for a first robotic arm and a second path for a second robotic arm 806 — Cause the first robotic arm to move a transducer along the first path 808 — Cause the second robotic arm to move a receiver along the second path 810 — Receive at least one image from the receiver

METHOD, DEVICE, AND SYSTEM FOR IMAGE GENERATION BASED ON CALCULATED ROBOTIC ARM POSITIONS

CROSS REFERENCE TO RELATED APPLICATIONS

This application claims the benefit of U.S. Provisional Application No. 63/088,372, filed on Oct. 6, 2020, and entitled "Method, Device, and System for Image Generation Based on Calculated Robotic Arm Positions", which application is incorporated herein by reference in its entirety.

FIELD

The present technology is related generally to obtaining images and, more particularly, to obtaining images based on calculated or known robotic arm positions.

BACKGROUND

Images obtained prior to and/or during a surgical operation may be used to perform registration prior to the surgical operation, verify registration during the surgical operation, and/or to determine movement of an anatomical feature of the patient. The images may be obtained throughout the surgical operation and may require activation of an imaging device multiple times during the operation.

SUMMARY

Embodiments of the present disclosure advantageously provide for obtaining images from known positions and orientations, such that the images may be used to update an existing 3D model and/or verify the accuracy of a registration throughout a surgical operation, such that up-to-date information is provided to a surgeon and/or a surgical robot. Further, embodiments of the present disclosure beneficially prevent harmful exposure of the patient to multiple iterations of radiation.

Example aspects of the present disclosure include:

A method for obtaining time of flight images according to one embodiment of the present disclose comprises: receiving a surgical plan; determining, based on the surgical plan, a first path for a first robotic arm and a second path for a second robotic arm; causing the first robotic arm to move on the first path, the first robotic arm configured to hold a transducer; causing the second robotic arm to move on the second path, the second robotic arm configured to hold a receiver; and receiving at least one image from the receiver, the image depicting patient anatomy and generated using time-of-flight measurements.

Any of the aspects herein, further comprising calculating a required pressure amplitude setting for the receiver.

Any of the aspects herein, wherein the first robotic arm moves on the first path synchronously to the second robotic arm moving on the second path.

Any of the aspects herein, wherein the at least one image is a three-dimensional model.

Any of the aspects herein, wherein the surgical plan includes information about a region of interest of the patient anatomy, and further wherein determining the first path and the second path is based on the information.

Any of the aspects herein, wherein the transducer is a first transducer, the method further comprising: determining a third path for a third robotic arm; and causing the third robotic arm to move on the third path, the third robotic arm holding a second transducer, wherein the first transducer has an image setting different from the second transducer.

Any of the aspects herein, wherein the image setting is at least one of a frequency and/or an amplitude.

Any of the aspects herein, wherein the image is an elastographic image.

Any of the aspects herein, wherein each of the first path and the second path is at least one of or a combination of an intra-corporeal path or an extra-corporeal path.

Any of the aspects herein, wherein each of the first path and the second path is at least one of or a combination of circular, parallel, or free-shaped.

A device for obtaining time of flight images based on a surgical plan according to one embodiment of the present disclosure comprises: at least one processor; and at least one memory storing instructions for execution by the at least one processor that, when executed, cause the at least one processor to: receive a surgical plan; determine, based on the surgical plan, a first path for a first robotic arm and a second path for a second robotic arm; cause the first robotic arm to move on the first path, the first robotic arm holding a transducer; cause the second robotic arm to move on the second path, the second robotic arm holding a receiver; and receive at least one image from the receive, the image depicting patient anatomy and generated using time-of-flight measurements Any of the aspects herein, wherein the memory stores further data for processing by the processor that, when processed, causes the processor to calculate a required pressure amplitude setting for the receiver.

Any of the aspects herein, wherein the first robotic arm moves on the first path synchronously with the second robotic arm moving on the second path.

Any of the aspects herein, wherein the at least one image is a three-dimensional model.

Any of the aspects herein, wherein the surgical plan includes information about a region of interest of the patient anatomy, and further wherein determining the first path and the second path is based on the information.

Any of the aspects herein, wherein the transducer is a first transducer, and wherein the memory stores further data for processing by the processor that, when processed, causes the processor to: determine a third path for a third robotic arm; and cause the third robotic arm to move on the third path, the third robotic arm holding a second transducer, wherein the first transducer has an image setting different from the second transducer.

Any of the aspects herein, wherein the image setting is at least one of a frequency and/or an amplitude.

Any of the aspects herein, wherein the image is an elastographic image.

Any of the aspects herein, wherein each of the first path and the second path is at least one of or a combination of an intra-corporeal path or an extra-corporeal path.

A system for obtaining time of flight images based on a surgical plan according to one embodiment of the present disclosure comprises: an imaging device comprising a transducer and a receiver; a plurality of robotic arms, a first robotic arm of the plurality of robotic arms configured to hold the transducer and a second robotic arm of the plurality of robotic arms configured to hold the receiver; at least one processor; and at least one memory storing instructions for execution by the at least one processor that, when executed, cause the at least one processor to: receive a surgical plan; determine, based on the surgical plan, a first path for a first robotic arm and a second path for a second robotic arm; cause the first robotic arm to move on the first path, the first robotic arm holding a transducer; cause the second robotic arm to move on the second path, the second robotic arm holding a receiver; and receive at least one image from the receiver, the image depicting patient anatomy and generated using time-of-flight measurements.

A method for updating a three-dimensional (3D) model of a patient anatomy according to one embodiment of the present disclosure comprises: receiving a 3D model of a patient anatomy; calculating one or more poses for an imaging device to image an anatomical feature, based on the 3D model of the patient anatomy; receiving an image from the imaging device at each of the one or more poses to yield an image set for the anatomical feature; and updating a representation of the anatomical feature in the 3D model of the patient anatomy based on at least one image from the image set and the pose corresponding to the at least one image to yield an updated 3D model of the patient anatomy.

Any of the aspects herein, wherein calculating the one or more poses for the imaging device includes calculating movements of a robotic arm holding the imaging device.

Any of the aspects herein, wherein the robotic arm has at least five degrees of freedom of movement.

Any of the aspects herein, wherein the robotic arm holding the imaging device has at least six degrees of freedom of movement.

Any of the aspects herein, wherein the imaging device is a first imaging device and the image set may be a first image set.

Any of the aspects herein, further comprising: receiving an image from a second imaging device imaging device at one or more poses to yield a second image set for the anatomical feature, and updating the representation of the anatomical feature in the 3D model of the patient anatomy is further based on at least one image from the second image set and the pose corresponding to that image to yield the updated 3D model of the patient anatomy.

Any of the aspects herein, wherein the first imaging device is an ultrasound probe and the second imaging device is an optical coherence tomography camera.

Any of the aspects herein, wherein the first imaging device is held by a first robotic arm and the second imaging device is held by a second robotic arm.

Any of the aspects herein, wherein updating the representation of the anatomical feature in the 3D model of the patient anatomy comprises adding soft tissue data to the 3D model of the patient anatomy.

Any of the aspects herein, wherein the soft tissue data is obtained from an optical coherence tomography camera.

Any of the aspects herein, wherein calculating the one or more poses is based on one or more characteristics of the imaging device.

Any of the aspects herein, wherein the 3D model of the patient anatomy includes one or more artifacts, the one or more poses may be calculated based on the one or more artifacts, and the updated 3D model of the patient anatomy may not include the one or more artifacts.

Any of the aspects herein, wherein the one or more poses for the imaging device forms a first set of poses for the imaging device.

Any of the aspects herein, further comprising: calculating a second set of poses for the imaging device; receiving an updated image from the imaging device at each pose of the second set of poses to yield an updated image set; and updating the updated 3D model of the patient anatomy using at least one updated image from the updated image set and based on the pose from the second set of poses corresponding to the at least one updated image.

Any of the aspects herein, wherein updating the updated 3D model of the patient anatomy occurs when the updated 3D model is determined to be missing information.

Any of the aspects herein, wherein at least one pose of the second set of poses matches at least one pose of the first set of poses.

Any of the aspects herein, further comprising comparing at least one updated image from the updated image set with at least one image of the image set to identify movement of an anatomical feature depicted in the at least one image.

Any of the aspects herein, further comprising determining at least one of a position and an orientation of the anatomical feature based at least in part on the updated image.

Any of the aspects herein, wherein the imaging device is a first imaging device and the method further comprises: obtaining at least a first one of the images with the first imaging device held by the robotic arm in a corresponding first one of the one or more poses; and obtaining at least a second one of the images with a second imaging device held by the robotic arm in a corresponding second one of the one or more poses.

Any of the aspects herein, wherein the robotic arm is a first robotic arm and the imaging device includes an emitter held by the first robotic arm.

Any of the aspects herein, wherein the imaging device further includes a detector held by a second robotic arm having at least five degrees of freedom of movement.

Any of the aspects herein, wherein the one or more poses for the imaging device to image the anatomical feature includes one or more poses for both the emitter and the detector.

Any of the aspects herein, wherein the imaging device is a first imaging device and the robotic arm is a first robotic arm.

Any of the aspects herein, wherein the first imaging device obtains a first one of the images independently of a second imaging device held by a second robotic arm obtaining a second one of the images.

A device for updating a three-dimensional (3D) model according to at least one embodiment of the present disclosure comprises: at least one processor; and at least one memory storing instructions for execution by the at least one processor that, when executed, cause the at least one processor to: receive a 3D model of a patient anatomy; calculate one or more poses for an imaging device to image an anatomical feature, based on the 3D model of the patient anatomy; receive an image from the imaging device at each of the one or more poses to yield an image set for the anatomical feature; and update a representation of the anatomical feature in the 3D model of the patient anatomy based on at least one image from the image set and the pose corresponding to the at least one image to yield an updated 3D model of the patient anatomy.

A system for updating a three-dimensional (3D) model according to at least one embodiment of the present disclosure comprises: at least one imaging device; a plurality of robotic arms, at least one arm of the plurality of robotic arms configured to hold the at least one imaging device; at least one processor; and at least one memory storing instructions for execution by the at least one processor that, when executed, cause the at least one processor to: receive a 3D model of a patient anatomy; calculate one or more poses for the at least one imaging device to image an anatomical feature, based on the 3D model of the patient anatomy; receive an image from the at least one imaging device at each of the one or more poses to yield an image set for the anatomical feature; and update a representation of the anatomical feature in the 3D model of the patient anatomy based on at least one image from the image set and the pose corresponding to the at least one image to yield an updated 3D model of the patient anatomy.

Any of the aspects herein, wherein the at least one imaging device comprises a plurality of imaging devices and the at least one arm of the plurality of robotic arms is configured to selectively hold each of the plurality of imaging devices.

Any of the aspects herein, wherein the at least at least one arm of the plurality of robotic arms is configured to move the at least one imaging device to the one or more poses.

Any of the aspects herein, wherein the plurality of robotic arms comprises a first arm and a second arm.

Any of the aspects herein, wherein the first arm is configured to pose a first one of the at least one imaging device independently of the second arm positioning a surgical tool or a second one of the at least one imaging device.

A method for obtaining images based on a surgical plan according to at least one embodiment of the present disclosure comprises: receiving a surgical plan; identifying image information for the surgical plan; determining a pose for an imaging device to obtain the identified image information; determining at least one setting of the imaging device to obtain the identified image information based on the plan and the pose; and receiving an image from the identified imaging device at the determined pose using the determined at least one setting.

Any of the aspects herein, further comprising: extracting the identified image information for the surgical plan from the obtained image.

Any of the aspects herein, wherein the image is obtained prior to carrying out the surgical plan.

Any of the aspects herein, wherein the image is obtained between two steps of the surgical plan.

Any of the aspects herein, wherein determining the at least one setting is based on at least one characteristic of the imaging device or the surgical plan.

Any of the aspects herein, further comprising: calculating, based on the surgical plan, at least one predicted movement of an anatomical feature depicted in the image; determining an updated pose for the imaging device based on the predicted movement; receiving an updated image from the imaging device at the updated pose; and verifying the predicted movement based on a comparison of the updated image and the corresponding image.

Any of the aspects herein, further comprising: determining at least one updated setting for the imaging device, wherein the updated image reflects use of the at least one updated setting.

Any of the aspects herein, wherein the updated pose matches the pose.

Any of the aspects herein, further comprising: identifying new information about the anatomical feature based on the updated image.

Any of the aspects herein, wherein the new information includes one or more of a change in a position and/or an orientation of the anatomical feature, a change in a surface characteristics of the anatomical feature, a change in a size of the anatomical feature, or an engagement of the anatomical feature with a surgical implant.

Any of the aspects herein, wherein the surgical plan comprises information about at least one artifact.

Any of the aspects herein, wherein the pose may is calculated based on the information, and the obtained image does not include the at least one artifact.

Any of the aspects herein, wherein the surgical plan comprises a three-dimensional (3D) model of a patient anatomy and the method further comprises updating the 3D model based on the obtained image and based on the corresponding pose to yield an updated 3D model.

Any of the aspects herein, wherein determining the pose is further based on the 3D model.

Any of the aspects herein, wherein the 3D model includes information about one or more artifacts, the pose is calculated based on the information, and the obtained image does not include the one or more artifacts.

Any of the aspects herein, wherein calculating the pose is based on one or more characteristics of the imaging device. At least one robotic arm may support the imaging device in the pose.

A method for obtaining images based on a surgical plan according to at least one embodiment of the present disclosure comprises: receiving a surgical plan; identifying image information for the surgical plan; determining at least one setting of an imaging device to obtain the identified image information based on the plan; determining a pose for the imaging device to obtain the identified image information based on the plan and the at least one setting; and receiving an image from the imaging device at the determined pose using the determined at least one setting.

A method for obtaining images based on a surgical plan according to at least one embodiment of the present disclosure comprises: calculating, based on the surgical plan, at least one predicted movement of an anatomical feature depicted in a first image; determining a pose for the imaging device based on the predicted movement; receiving a second image from the imaging device at the pose; and verifying the predicted movement based on a comparison of the second image and the first image.

A method for obtaining images based on a surgical plan according to at least one embodiment of the present disclosure comprises: receiving a surgical plan; identifying image information for the surgical plan; receiving setting information about at least one setting of an imaging device; determining a pose for the imaging device to obtain the identified image information based on the surgical plan and the setting information; and receiving an image from the imaging device at the determined pose using the at least one setting.

A device for obtaining images based on a surgical plan according to at least one embodiment of the present disclosure comprises: at least one processor; and at least one memory storing instructions for execution by the at least one processor that, when executed, cause the at least one processor to: receive a surgical plan; identify image information for the surgical plan; determine a pose for an imaging device to obtain the identified image information; determine at least one setting of the imaging device to obtain the identified image information based on the plan and the pose; and receive an image from the identified imaging device at the determined pose using the determined at least one setting.

A system for obtaining images based on a surgical plan according to at least one embodiment of the present disclosure comprises: at least one imaging device; a plurality of robotic arms, at least one arm of the plurality of robotic arms configured to hold the at least one imaging device; at least one processor; and at least one memory storing instructions for execution by the at least one processor that, when executed, cause the at least one processor to: receive a surgical plan; identify image information for the surgical plan; determine a pose for the at least one imaging device to obtain the identified image information; determine at least one setting of the at least one imaging device to obtain the identified image information based on the plan and the pose; and receive an image from the identified imaging device at the determined pose using the determined at least one setting.

Any of the aspects herein, wherein the at least one imaging device comprises a plurality of imaging devices and the at least one arm may be configured to selectively hold each of the plurality of imaging devices.

Any of the aspects herein, wherein the at least one arm is configured to move the at least one imaging device to the one or more poses.

Any of the aspects herein, wherein the plurality of robotic arms comprises a first arm and a second arm and the method further comprises: obtaining at least a first image with a first imaging device held by the first arm in one of the one or more poses; and obtaining at least a second image with a second imaging device held by the first arm or the second arm in another one of the one or more poses.

Any of the aspects herein, wherein the plurality of arms comprises a first arm and a second arm, the at least one imaging device comprises a first imaging device and a second imaging device, and the first arm is configured to position the first imaging device independently of the second arm positioning a surgical tool or the second imaging device.

A method for model registration according to at least one embodiment of the present disclosure comprises: receiving a 3D model of an anatomical portion of a patient; calculating one or more poses of at least one imaging device based on the 3D model; receiving an image from the at least one imaging device at each of the one or more poses to yield an image set, each image depicting at least one anatomical feature of the patient; aligning, based at least in part on the one or more poses, the at least one anatomical feature in each image with a corresponding anatomical feature in the 3D model; and registering an image space to a patient space based on the alignment.

Any of the aspects herein, wherein calculating the one or more poses of the at least one imaging device includes calculating movements of a robotic arm holding the at least one imaging device.

Any of the aspects herein, wherein the robotic arm has at least five degrees of freedom of movement.

Any of the aspects herein, further comprising causing a robotic arm to orient the imaging device at each of the one or more poses.

Any of the aspects herein, wherein the at least one imaging device does not emit ionizing radiation.

Any of the aspects herein, wherein the aligning uses one or more of feature recognition, artificial intelligence, machine learning, or pose information.

Any of the aspects herein, further comprising verifying the registration by evaluating the alignment, and determining that the registration is invalid when the alignment reveals a discrepancy between an imaged position of an anatomical feature and a position of the anatomical feature in the 3D model.

Any of the aspects herein, wherein the image set is a first image set and the method further comprises: obtaining an updated image from the at least one imaging device at one or more of the poses to yield a second image set; and comparing each updated image in the second image set with a corresponding image from the first image set to determine movement of the anatomical feature.

Any of the aspects herein, wherein the image space is reregistered to the patient space based on the second image set.

Any of the aspects herein, wherein the 3D model is created with a first image modality and the at least one imaging device is a second image modality different than the first image modality.

Any of the aspects herein, wherein the at least one imaging device is an ultrasound probe or an optical coherence tomography camera.

Any of the aspects herein, wherein a detector of the ultrasound probe and an emitter of the ultrasound probe are each held a distance from and opposite each other by separate robotic arms and the method further comprises determining a time of flight of an ultrasound signal based on the distance and a duration between emission of the signal by the emitter and detection of the signal by the detector.

Any of the aspects herein, wherein registering the first image space to the patient space occurs without a fiducial marker.

A device for model registration according to at least one embodiment of the present disclosure comprises: at least one processor; and at least one memory storing instructions for execution by the at least one processor that, when executed, cause the at least one processor to: receive a 3D model of an anatomical portion of a patient; calculate one or more poses of at least one imaging device based on the 3D model; receive an image from the at least one imaging device at each of the one or more poses to yield an image set, each image depicting at least one anatomical feature of the patient; align, based at least in part on the one or more poses, the at least one anatomical feature in each image with a corresponding anatomical feature in the 3D model; and register an image space to a patient space based on the alignment.

A method for registration verification according to at least one embodiment of the present disclosure comprises: calculating one or more first poses for an imaging device; calculating one or more second poses for the imaging device; receiving a first image from an imaging device, during a first time period, at each of the one or more first poses to yield a first image set, each first image depicting at least one anatomical feature; and receiving a second image from an imaging device, during a second time period after the first time period, at each of the one or more second poses to yield a second image set, each second image depicting at least one anatomical feature.

Any of the aspects herein, wherein the calculating one or more first poses is based at least in part on information about the patient's anatomy.

Any of the aspects herein, wherein the calculating one or more second poses is based at least in part on a surgical plan.

Any of the aspects herein, further comprising: determining, based on the first image set and the second image set, whether an anatomical feature depicted in one or more of the first images and in one or more of the second images remained in the same pose from the first time period to the second time period.

A system for model registration according to at least one embodiment of the present disclosure comprises: at least one imaging device; a plurality of robotic arms, at least one arm of the plurality of robotic arms configured to hold the at least one imaging device; at least one processor; and at least one memory storing instructions for execution by the at least one processor that, when executed, cause the at least one processor to: receive a 3D model of an anatomical portion of a patient; calculate one or more poses of the at least one imaging device based on the 3D model; receive an image from the at least one imaging device at each of the one or more poses to yield an image set, each image depicting at least one anatomical feature of the patient; align, based at least in part on the one or more poses, the at least one anatomical feature in each image with a corresponding anatomical feature in the 3D model; and register an image space to a patient space based on the alignment.

Any of the aspects herein, wherein the at least one imaging device comprises a plurality of imaging devices and the at least one arm of the plurality of robotic arms is configured to selectively hold each of the plurality of imaging devices.

Any of the aspects herein, wherein the at least one arm of the plurality of robotic arms is configured to move the at least one imaging device, in sequence, to the one or more poses.

Any of the aspects herein, wherein the plurality of robotic arms comprises a first arm and a second arm and the system further comprises obtaining at least one of the second images with a first imaging device held by the first arm in one of the one or more poses; and obtaining at least another one of the second images with a second imaging device held by the first arm or the second arm in another one of the one or more poses.

Any of the aspects herein, wherein the plurality of arms comprises a first arm and a second arm, and the first arm is configured to position a first one of the at least one imaging device independently of the second arm positioning a surgical tool or a second one of the at least one imaging device.

The details of one or more aspects of the disclosure are set forth in the accompanying drawings and the description below. Other features, objects, and advantages of the techniques described in this disclosure will be apparent from the description and drawings, and from the claims.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (e.g., $X_1$ and $X_2$) as well as a combination of elements selected from two or more classes (e.g., $Y_1$ and $Z_o$).

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

Numerous additional features and advantages of the present invention will become apparent to those skilled in the art upon consideration of the embodiment descriptions provided hereinbelow.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 4 is an additional flowchart of a method according to at least one embodiment of the present disclosure;

FIG. 5 is another flowchart of a method according to at least one embodiment of the present disclosure;

DETAILED DESCRIPTION

Figure 1:
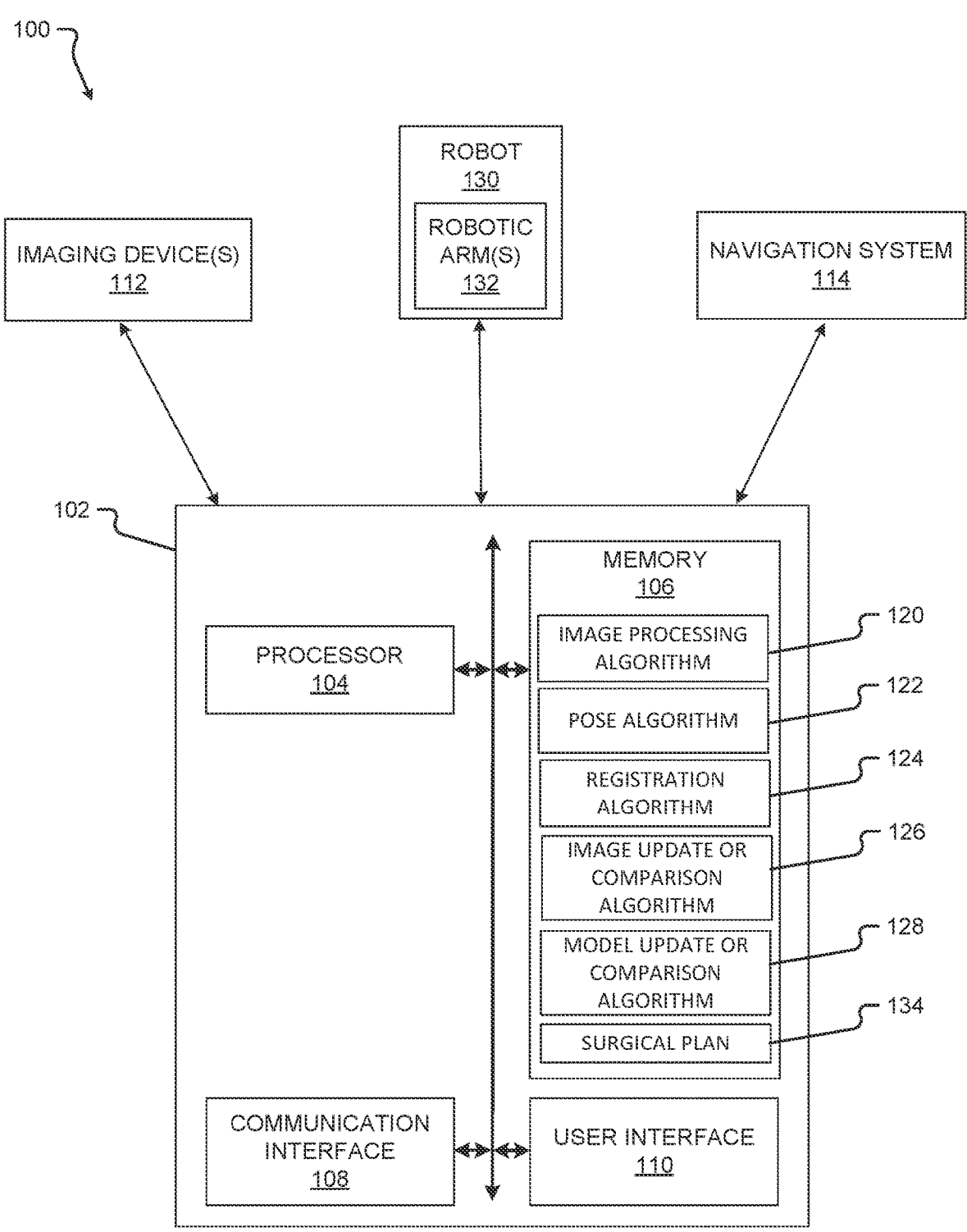
FIG. 1 is a block diagram of a system according to at least one embodiment of the present disclosure.

It should be understood that various aspects disclosed herein may be combined in different combinations than the combinations specifically presented in the description and accompanying drawings. It should also be understood that, depending on the example or embodiment, certain acts or events of any of the processes or methods described herein may be performed in a different sequence, and/or may be added, merged, or left out altogether (e.g., all described acts or events may not be necessary to carry out the disclosed techniques according to different embodiments of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any embodiments of the disclosure are explained in detail, it is to be understood that the disclosure is not limited in its application to the details of construction and the arrangement of components set forth in the following description or illustrated in the drawings. The disclosure is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

In some applications, imaging devices may be used to obtain images prior to or during a surgical operation. However, in some situations, the imaging devices may expose a patient, in particular, pediatric patients, to harmful radiation multiple times throughout the operation. In other applications, images taken during the surgical operation may be difficult to correlate or match to a preoperative image. Such difficulty may result in increased operating time as the images are manually or iteratively matched to the preoperative image. In further applications, imaging devices typically used during robotic surgery are optimized for imaging hard tissue or soft tissue but not both, and are thus limited to certain types of operations. Several of the embodiments discussed herein provide improved imaging using a robotic system and improved registration verification and/or image updating during an operation.

Also, existing imaging devices used for registration and associated imaging, such as O-arms and C-arms, tend to be large and bulky. Use of such devices may require removing from the patient and/or from the operating table one or more devices, tools, markers, and/or other objects being used in the surgical procedure. As a result, use of such devices—particularly after a surgical procedure commences—is disfavored. The time required to complete a re-registration procedure using such devices is not insignificant, particularly when a space for the imaging device must be cleared so that the imaging device can be properly positioned to obtain the needed image(s). Moreover, given the longer a surgical procedure lasts, the more expensive the procedures become (whether in terms of actual cost, opportunity cost, and/or impact on the patient).

One challenge during navigated and robotic spinal surgery is that a vertebra may move during surgery due to surgical activity or patient movement, which may negatively impact the accuracy of a registration performed at an earlier stage of surgery. A secondary navigation reference frame may be used to warn against such movement. However, these frames are invasive and bulky, and their use is limited to a single remote location.

A non-invasive system and method for registration verification with no or minimal impact on a surgeon's access to the surgical field is provided. The system includes a robotic arm, an ultrasound probe, and a control unit. During initial registration, the system accurately brings the ultrasound probe to one or more positions and records sonographic images from these positions. Before registration-sensitive steps, the robotic system retakes ultrasound or sonographic images from the same positions and compares them to the registration-time images for evidence of registration impact.

Embodiments of the present disclosure may comprise calculating effective and feasible ultrasonic (or other imaging modality) imaging positions from an initial 3D scan (e.g., a CT or ultrasound scan) and/or a surgical plan; accurately positioning an ultrasound or other imaging probe in a desired position and orientation (i.e., pose); implementing an ultrasound (or other imaging modality) recording sequence immediately after registration; implementing the ultrasound (or other imaging modality) recording sequence before a registration-dependent step; and/or comparing two recorded images for evidence of movement.

In some embodiments, the system may provide an updated local registration matrix based on a local 3D reconstruction.

Such reliable registration accuracy monitoring enables support for advanced robotic use cases including, for example, decompression, long constructs, and non-general anesthesia procedures.

Another challenge associated with surgery, including, for example, spinal surgeries for pediatric patients, is radiation exposure caused by methods involving a CT scan and a fluoroscopy or an intraoperative CT scan. Thus, a radiation-free method for pediatric spine surgery, as one example, is desirable. Ultrasound is one type of radiation-free imaging modality that may be used for registration, but ultrasound is limited to narrow visibility windows allowed bony structures and may require manual landmark identification or co-identified fiducials.

Embodiments of a radiation-free workflow or method as described herein includes using a preoperative MRI scan for procedural planning (which may involve the use of bone-enhancement methods). During surgery, a robot-manipulated ultrasound probe (or other imaging probe) is used to scan the spinal area. The ultrasound probe (or other imaging probe) is moved along a 3-dimensional path utilizing the robot's multiple (e.g., seven) degrees of freedom, which path is calculated to maximize spinal anatomy details available through the vertebral structures. One or more additional paths, or modifications to the path, may be iteratively calculated to address any remaining ambiguities of the spinal area. This workflow or method is thus free of radiation and free of landmarks and/or fiducials. Although described above with respect to a spinal procedure, a similar workflow or method may be used for imaging other portions of the anatomy.

Images captured with the ultrasound probe may be used for iterative 3D reconstruction of a pre-operative model. Methods to resolve grey level for each voxel and geometric distance disagreements from differing projections and distances may be utilized as part of the reconstruction. Registration ambiguities may be resolved by iterative evaluation thereof and calculation of additional ultrasound images needed to resolve the same. In some embodiments, two robotic arms may be used to employ time-of-flight or absorption-based ultrasound imaging, by placing the source and detector each on a separate robotic arm.

Three-dimensional ultrasound imaging may require large and expensive probes to reconstruct limited volumes depending on the used frequencies and probes. In many clinical scenarios, the need arises to generate 3D ultrasound images for irregularly shaped volumes or volumes that are larger than the ultrasonic covered footprint. Such imaging may be required to occur through limited visualization ports and with small orifices. Further, 3D reconstruction methods may require fiducial markers or may be limited to methods that utilize or allow limited if any probe movement.

Various solutions free of imaged volume preparation or tagging, or specific probe technology are described herein. In one embodiment, for example, a system comprises a control unit and one or more robotic arms with accurate positional sensing and multiple (e.g., seven) degrees of freedom. Each arm holds an imaging ultrasonic probe (or other imaging probe or device). Each sonographic (or other) probe may be 2D or 3D, A-line, linear, curved, or comprise a phased array. During use, a user indicates a volume to image. In some embodiments, the system may incorporate optical 3D cameras allowing body surface reconstructions. In other embodiments, the body contour may be provided by co-registered 3D imaging (e.g., CT or MRI imaging). The system calculates probe movement paths covering the targeted volume based on the known characteristics of each imaging probe. The paths may be verified to conform to the skin, if external. The system causes the robotic arm(s) to move the probes around the volume of interest, and reconstructs a 3D image based on the known gray scale determinants from each probe. The system may also identify missing areas in the reconstructed volume and calculate one or more paths for the probes to provide the missing information. The system also may assign a normalized gray scale value for each voxel and a calibration process may be applied to each probe.

In sonographic imaging, in order to obtain a very high-resolution image, one needs to apply a relatively high ultrasonic frequency, and the resulting imaging depth is relatively limited. For example, in relation to spine surgery, the probe must be fairly close to the bone. This may be problematic near bony structure, as the high frequency ultrasonic waves might cause heating of the bone and adjacent tissues to a degree that might cause tissue damage.

Optical Coherence Tomography (OCT) is a real-time imaging technique with very high-resolution capabilities. This technique is based on visible light, and is therefore ionizing-radiation free and does not cause tissue heating. For example, a robotic controlled arm equipped with OCT imaging equipment might perform imaging close to bony structures, without negatively heating the area, as would be the case with ultrasonic imaging, while gaining superior image resolution. Additionally, by taking multiple images, with known precise locations and orientations of the OCT camera or probe (due to the use of the robotic controlled arm), multiple images may be registered and used to generate a 3D volume reconstruction of an imaged object.

A system according to some embodiments of the present disclosure therefore includes a robotic system with a robotic arm holding an OCT camera and a control unit. The system places the OCT camera adjacent to the tissue to be imaged.

The OCT camera may beneficially provide very detailed imaging information of any structure, organs, and/or blood vessels in the field of view of the OCT camera. For example, using the OCT camera images, the system can determine an exact depth of bone, within the tissue, for a more accurate penetration of other robotic controlled tools, or warn if there is a blood vessel nearby. The system can generate continuous real-time imaging for any desirable amount of time, with superior image quality and without radiation or heating concerns. The system can also generate 2D images, or even reconstruct 3D volumes, as it has the exact location and orientation of the OCT camera (due to use of the robotic arm) for each of the 2D images to complete a 3D volume rendering or reconstruction.

In other applications of sonographic imaging, the transducer and the receiver may be positioned opposite each other to obtain Time of Flight (ToF) images. ToF for sound waves provides a quick, radiation free, contrast free, and information-unique tissue sensitive imaging technique. Using various scan techniques, (such as ToF imaging, in addition to echo imaging) can add various sources of information. Compared with echo imaging, ToF imaging may be less sensitive to high-attenuation elements (e.g., bone) as with ToF imaging the wave only passes through the anatomical elements once, and not twice (as with echo imaging), hence its attenuation is reduced. In other words, with echo imaging high-attenuation elements (e.g., bones) may "mask" elements located behind them, whereas with ToF imaging, anatomical elements behind the high-attenuation elements (e.g., bones) may be captured, and seen in the final reconstructed image. ToF measurements tend to require accurate positioning of the transducer and the receiver opposite each other while maintaining an air-free (or substantially air-free) path. Three-dimensional ToF may further require simultaneous movements of the transducer and the receiver. The movement paths for a body or organ surface may be non-circular. The non-circular path may be another advantage, as it may reduce the signal attenuation, where possible, providing a better signal to noise ratio, and better clinical image outcome.

A system according to some embodiments of the present disclosure for 3-D ToF computed tomography (CT) therefore may include a control unit and a robotic system with at least two arms, wherein one of the arms holds a transducer and another one of the arms holds the receiver. The system may compute a scanning movement plan based on a registered pre-acquired scan or a real-time optical scan and an indication of a region of interest. The system may use intra-or extra-corporeal paths, or a combination of intra- and extra-corporeal paths. The system may use circular, parallel or free-shaped paths. The frequencies to be used may be selected by the user or recommended by the system based on known tissue composition. The system may calculate the required pressure amplitude to achieve the needed penetration of the sound waves. The system may synchronously move the transducer and the receiver along the scanned body. The system may also perform 2D or 3D reconstruction as described in some embodiments of the present disclosure. In some embodiments, the system may also provide elastographic imaging or other sonographic imaging techniques such as ultrasound phase contrast (for the detection of slowly varying structures within the body or thermal imaging) or the measurement of the Acoustic Nonlinearity Parameter, or ultrasonic doppler imaging In some embodiments, the system may provide any type of imaging with concurrent use of multiple transducers with different frequencies and amplitudes.

Turning first to FIG. 1, a block diagram of a system 100 according to at least one embodiment of the present disclosure is shown. The system 100 may be used to obtain and process image data; execute one or more of the methods described herein; execute an image processing algorithm, a pose algorithm, a registration algorithm, an image update or comparison algorithm, and/or a model update or comparison algorithm; and/or carry out one or more other aspects of one or more of the methods disclosed herein. The system 100 comprises a computing device 102, one or more imaging devices 112, a navigation system 114, and/or a robot 130. Systems according to other embodiments of the present disclosure may comprise more or fewer components than the system 100. For example, the system 100 may not include the navigation system 114, or one or more components of the computing device 102.

The computing device 102 comprises a processor 104, a memory 106, a communication interface 108, and a user interface 110. Computing devices according to other embodiments of the present disclosure may comprise more or fewer components than the computing device 102.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging device 112, the robot 130, and/or the navigation system 114.

The memory 106 may be or comprise RAM, DRAM, SDRAM, other solid-state memory, any memory described herein, or any other tangible, non-transitory memory for storing computer-readable data and/or instructions. The memory 106 may store information or data useful for completing, for example, any step of the methods 200, 300, 400, 500, 600, 700 or 800 described herein, or of any other methods. The memory 106 may store, for example, one or more image processing algorithms 120, one or more pose algorithms 122, one or more registration algorithms 124, one or more image update or comparison algorithms 126, one or more model update or comparison algorithm 128, and/or one or more surgical plans 134. Such instructions or algorithms may, in some embodiments, be organized into one or more applications, modules, packages, layers, or engines. The algorithms and/or instructions may cause the processor 104 to manipulate data stored in the memory 106 and/or received from the imaging device 112 and/or the robot 130.

The computing device 102 may also comprise a communication interface 108. The communication interface 108 may be used for receiving image data or other information from an external source (such as the imaging device 112, the navigation system 114, and/or the robot 130), and/or for transmitting instructions, images, or other information to an external system or device (e.g., another computing device 102, the navigation system 114, the imaging device 112, and/or the robot 130). The communication interface 108 may comprise one or more wired interfaces (e.g., a USB port, an ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some embodiments, the communication interface 108 may be useful for enabling the device 102 to communicate with one or more other processors 104 or computing devices 102, whether to reduce the time needed to accomplish a computing-intensive task or for any other reason.

The computing device 102 may also comprise one or more user interfaces 110. The user interface 110 may be or comprise a keyboard, mouse, trackball, monitor, television, touchscreen, and/or any other device for receiving information from a user and/or for providing information to a user. The user interface 110 may be used, for example, to receive a user selection or other user input regarding receiving image data, one or more images, and/or one or more 3D models; to receive a user selection or other user input regarding receiving a surgical plan; to receive a user selection or other user input regarding determining a first pose for a first robotic arm and a second pose for a second robotic arm; to receive a user selection or other user input regarding identifying image information needed to carry out a surgical plan; to receive a user selection or other user input regarding identifying an imaging device 112 needed to obtain the identified image information; to receive a user selection or other user input regarding determining at least one setting of the identified imaging device 112; to receive a user selection or other user input regarding calculating one or more poses of the imaging device 112; to receive a user selection or other user input regarding calculating one or more second poses; to receive a user selection or other user input regarding determining one or more poses for imaging device 112; to receive a user selection or other user input regarding causing the first robotic arm to position a transducer at the first pose; to receive a user selection or other user input regarding causing the second robotic arm to position a receiver at the second pose; to receive a user selection or other user input regarding causing imaging device 112 to obtain an image at each of the one or more poses; to receive a user selection or other user input regarding causing the identified imaging device 112 to obtain an image at each of the one or more poses using the determined at least one setting; to receive a user selection or other user input regarding receiving at least one image from the receiver, the at least one image depicting patient anatomy; to receive a user selection or other user input regarding receiving an image from the imaging device at each of the one or more poses to yield an image set for the anatomical feature; to receive a user selection or other user input regarding updating the 3D model based on at least one image from the image set obtained and the pose corresponding to the at least one image; to receive a user selection or other user input regarding aligning an anatomical feature in a second image(s) with a corresponding anatomical image in the first image(s); to receive a user selection or other user input regarding registering a first image space to a patient space; to receive a user selection or other user input regarding causing an imaging device 112 to obtain, during a first time period, a first image set; to receive a user selection or other user input regarding causing an imaging device 112 to obtain, during a second time period, a second image set; and/or to receive a user selection or other user input regarding displaying instructions for moving the imaging device 112 or causing the imaging device 112 to move. Notwithstanding the foregoing, each of the preceding inputs may be generated automatically by the system 100 (e.g., by the processor 104 or another component of the system 100) or received by the system 100 from a source external to the system 100. In some embodiments, the user interface 110 may be useful to allow a surgeon or other user to modify the instructions or other information displayed.

Although the user interface 110 is shown as part of the computing device 102, in some embodiments, the computing device 102 may utilize a user interface 110 that is housed separately from one or more remaining components of the computing device 102. In some embodiments, the user interface 110 may be located proximate one or more other components of the computing device 102, while in other embodiments, the user interface 110 may be located remotely from one or more other components of the computer device 102.

The imaging device 112 may be operable to image anatomical feature(s) (e.g., a bone, veins, tissue, etc.) and/or patient anatomy to yield image data (e.g., image data depicting or corresponding to a bone, veins, tissue, etc.). The image data may be first image data comprising pre-operative image data in some examples, image data obtained after a registration process in other examples, and/or image data obtained prior to or after a surgical step. The imaging device 112 may be capable of taking a 2D image or a 3D image to yield the image data. "Image data" as used herein refers to the data generated or captured by an imaging device 112, including in a machine-readable form, a graphical/visual form, and in any other form. In various examples, the image data may comprise data corresponding to an anatomical feature of a patient, or to a portion thereof. The imaging device 112 may be or comprise, for example, an ultrasound scanner, an O-arm, a C-arm, a G-arm, or any other device utilizing X-ray-based imaging (e.g., a fluoroscope, a CT scanner, or other X-ray machine), a magnetic resonance imaging (Mill) scanner, an optical coherence tomography scanner, an endoscope, a telescope, a thermographic camera (e.g., an infrared camera), or any other imaging device 112 suitable for obtaining images of an anatomical feature of a patient.

The imaging device 112 may additionally or alternatively be operable to image the anatomical feature to yield additional image data. The additional image data (which may be, for example, second image data or updated image data) may be obtained in real-time. The additional image data may be combined with previously obtained image data (e.g., first image data) to provide additional image information to the first image data or other previously obtained image data. In some embodiments, the imaging device 112 may comprise more than one imaging device 112. For example, a first imaging device may provide a first image set and a second imaging device may provide a second image set. Alternatively, a first imaging device may be used to obtain any image data described herein from a first pose or set of poses, and a second imaging device may be used to obtain any image data described herein from a second pose or set of poses. In still other embodiments, the same imaging device may be used to provide both the first image data and the second image data, and/or any other image data described herein.

In embodiments where the imaging device 112 is an ultrasound imaging device, various imaging techniques may be used to obtain ultrasound image data. The ultrasound imaging device may use a pulse-echo technique or a phase-contrast technique. The ultrasound imaging device may also use a nonlinearity ultrasonic parameter technique to obtain ultrasound image data.

The pulse-echo technique may be used when a solid boundary exists between two mediums such that an echo may be detected. The pulse-echo technique may also be used when a contrast agent is used for detection and may be beneficial when there is a high concentration of the contrast agent. The phase-contrast technique may be useful in multiple situations and is used to detect gradual changes in an ultrasonic wave path. It may be used to detect thermal changes, or other gradual differences within an anatomical element, such as an organ. The phase-contrast technique may be used when there is a gradual change in a patient's anatomy occurs and a solid boundary does not exist between two mediums. The phase-contract technique in such instances may be used to detect subtle differences within, for example, tissues. The phase-contrast technique may also be used when a contrast agent is used for detection and may be beneficial when a small amount of contrast agent is used in a fairly low concentration or in instances where the contrast agent is dissipating.

The navigation system 114 may provide navigation for a surgeon and/or a surgical robot during an operation. The navigation system 114 may be any now-known or future-developed navigation system, including, for example, the Medtronic StealthStation™ S8 surgical navigation system. The navigation system 114 may include a camera or other sensor(s) for tracking one or more reference markers, navigated trackers, or other objects within the operating room or other room in which some or all of the system 100 is located. In various embodiments, the navigation system 114 may be used to track a position and orientation (i.e., pose) of the imaging device 112 (or, more particularly, of a navigated tracker attached, directly or indirectly, in fixed relation to the imaging device 112). The navigation system 114 may include a display for displaying one or more images from an external source (e.g., the computing device 102, imaging device 112, or other source) or a video stream from the camera or other sensor of the navigation system 114. In some embodiments, the system 100 can operate without the use of the navigation system 114.

The robot 130 may be any surgical robot or surgical robotic system. The robot 130 may be or comprise, for example, the Mazor X™ Stealth Edition robotic guidance system. The robot 130 is configured to position the imaging device 112 at precise position(s) and orientation(s) and is advantageously capable of returning the imaging device 112 to the same position(s) and orientation(s) at a later point in time. The robot 130 may comprise one or more robotic arms 132. In some embodiments, the robotic arm 132 may comprise a first robotic arm and a second robotic arm, though the robot 130 may comprise more than two robotic arms. The first robotic arm may hold or otherwise support an imaging device 112 and the second robotic arm may hold or otherwise support another imaging device 112 or a surgical tool, and each robotic arm may be positionable independently of the other robotic arm. As a result, the first robotic arm may position the imaging device 112 independently of the position and orientation of the second robotic arm, and the second robotic arm may position the surgical tool or another imaging device 112 independently of the position and orientation of the first robotic arm. The imaging device 112 may be disposed on an end of the first robotic arm and/or the second robotic arm in some examples, while in other examples the imaging device 112 may be disposed on any portion of the first robotic arm, the second robotic arm, and/or the robot 130. In some embodiments, the robotic arm 132 is configured to selectively hold each of a plurality of imaging devices 112. For example, the robotic arm 132 may hold a first imaging device; remove, release, return, and/or store the first imaging device; and receive, pick up, or otherwise hold a second imaging device. In some embodiments, a plurality of imaging devices 112 may be stored in a magazine or other storage unit, and the robotic arm 132 may selectively pick up and use one or more of the plurality of imaging devices 112.

The robot 130, together with the robotic arm 132, may have, for example, at least five degrees of freedom. In some embodiments the robotic arm 132 has at least six degrees of freedom. In yet other embodiments, the robotic arm 132 may have less than five degrees of freedom. Further, the robotic arm 132 may be positioned or positionable in any pose, plane, and/or focal point. The pose includes a position and an orientation. As a result, an imaging device 112 or other object held by the robot 130 (or, more specifically, by the robotic arm 132) may be precisely positionable in one or more needed and specific positions and orientations.

In some examples, the imaging device 112 may be an ultrasound device having an ultrasound source and an ultrasound detector or receiver, and the robotic arm 132 may comprise a first robotic arm for supporting the ultrasound source and a second robotic arm for supporting the ultrasound detector or receiver at a known distance and orientation from the ultrasound source. The robotic arm 132 may be configured to hold an imaging device 112 and to position the imaging device 112 in a particular pose (i.e., a position and orientation). The robotic arm 132 may also be configured to move or position the imaging device 112 in various poses as calculated and described with respect to FIGS. 2, 4, 5, 6, 7 and 8 (corresponding to the methods 200, 400, 500, 600, 700 and 800) or one or more updated poses or second set of poses as calculated and described with respect to FIG. 3 (corresponding to the methods 300).

Reference markers (i.e., navigation markers) may be placed on the robot 130, the robotic arm 132, the imaging device 112, or any other object in the surgical space. The reference markers may be tracked by the navigation system 114, and the results of the tracking may be used by the robot 130 and/or by an operator of the system 100 or any component thereof. In some embodiments, the navigation system 114 can be used to track other components of the system (e.g., imaging device 112) and the system can operate without the use of the robot 130 (e.g., with the surgeon manually manipulating the imaging device 112, whether based on information and/or instructions generated by the navigation system 114 or otherwise).

The system 100 or similar systems may be used, for example, to carry out one or more aspects of any of the methods 200, 300, 400, 500, 600, 700 and/or 800 described herein. The system 100 or similar systems may also be used for other purposes. In some embodiments, for example, a system 100 may be used to generate a 3D model of an anatomical feature or an anatomical volume of a patient. For example, the robotic arm 132 (controlled by a processor of the robot 130, the processor 104 of the computing device 102, or some other processor, with or without any manual input) may be used to position the imaging device 112 at a plurality of predetermined, known poses, so that the imaging device 112 can obtain one or more images at each of the predetermined, known poses. Because the pose from which each image is taken is known, the resulting images may be assembled together to form or reconstruct a 3D model.

Construction or reconstruction of a 3D model in this manner may be facilitated by the use of a robot having a plurality of robotic arms 132 each holding an imaging device 112. Where each imaging device 112 is the same, the use of a plurality of imaging devices 112 enables more images to be taken in less time (both because each imaging device 112 can take images simultaneously or nearly simultaneously, and because each robotic arm 132 need only move the corresponding imaging device 112 to a subset of the total number of poses). Alternatively, the plurality of robotic arms 132 may hold a plurality of types of imaging devices 112 (e.g., one robotic arm 132 may hold an imaging device 112 configured to image hard tissue, and another robotic arm 132 may hold an imaging device 112 configured to image soft tissue), so that more information (e.g., information about both hard and soft tissue) may be included in the 3D model.

The system 100, when used to obtain images with an imaging device 112 from known positions and orientations (e.g., by using a robotic arm 132 to hold the imaging device 112 in one or more known poses, or by using the navigation system 114 to enable a surgeon or other user to hold the imaging device 112 in one or more known poses), beneficially enables a variety of methods and processes to be completed without the use of one or more of fiducials, markers, or image recognition software that are currently required to complete such methods and processes, thus reducing the time, expense, and complexity of such methods and processes. Moreover, the present disclosure is applicable to minimally invasive contexts, in that a robotic arm useful for minimally invasive surgery may hold an imaging device configured for use in a minimally invasive environment, and poses calculated by the processor 104 or any other processor may be constrained to be on one or more minimally invasive surgical paths.

Figure 2:
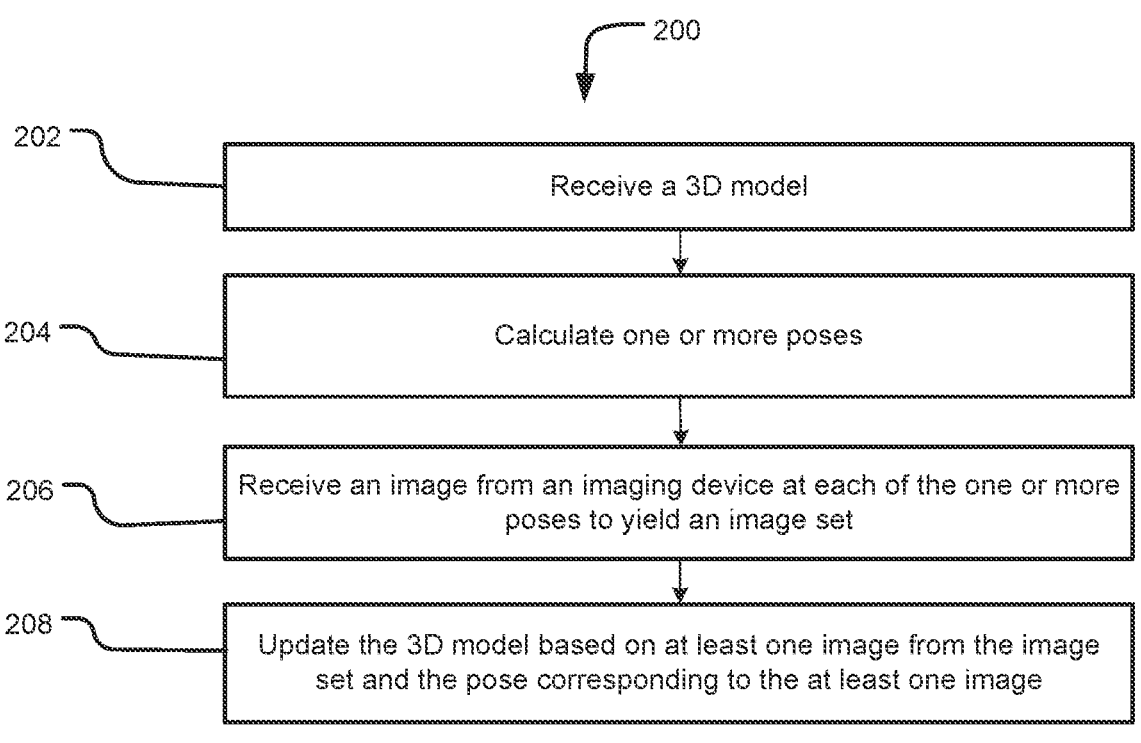
FIG. 2 is a flowchart of a method according to at least one embodiment of the present disclosure.

Turning now to FIG. 2, a method 200 for reconstructing or updating a three-dimensional (3D) model according to embodiments of the present disclosure may be executed, for example, in whole or in part, on a computing device such as the computing device 102 or similar device, and may utilize one or more other components of the system 100 or similar components. One or more aspects of the method 200 may be performed by or with a surgical robot, a surgeon, or a combination of both using one or more imaging devices such as the imaging device 112.

The method 200 may beneficially be used, for example, to reconstruct a 3D model generated from one or more images taken with a patient in a first position (e.g., a supine position) to reflect the patient's anatomy when the patient is in a different position (e.g., a prone position). Thus, for example, if a patient's spine is imaged using an MRI machine while the patient is lying in a supine position, but the patient will undergo a spinal surgical procedure while in the prone position, then a 3D model generated using the MRI image data may need to be reconstructed to reflect a slightly different position of the spinal vertebrae and/or one or more other anatomical features with the patient in the prone position. In this example and in related embodiments, the anatomical features themselves (e.g., each vertebra) may be expected to have the same shape, but a relative position or orientation between or among the anatomical features may be expected to have changed. The method 200, then, may be used to reconstruct the 3D model once the patient is positioned on the operating table, without having to utilize an O-arm, C-arm, MRI machine, or other bulky imaging device. Use of the method 200 in this situation beneficially enables the surgeon or other operator to initiate a surgical procedure with a currently accurate 3D model. Moreover, because a processor (e.g., the processor 104) can complete the reconstruction based on the known poses of the imaging device corresponding to each image obtained by the imaging device, the imaging device may be positioned as needed to maximize the amount of information that can be obtained from each image. In contrast to other reconstruction approach that may require an imaging device to be positioned in the same positions and orientations every time, without accounting for the unique anatomy of a given patient or for the specific information needed for the reconstruction.

The method 200 may also beneficially be used during a surgical procedure to update or reconstruct a 3D model of a relevant portion of a patient's anatomy based on changes resulting from the surgical procedure. For example, if one or more anatomical features have shifted during the procedure (whether as a result of the procedure itself or for any other reason), then the method 200 may be used to update or reconstruct the 3D model before continuing with the procedure. As another example, if one or more anatomical features have been changed by the procedure (e.g., by the removal of bony or soft tissue or otherwise), then the method 200 may be used to update or reconstruct the 3D model to reflect the change. As still another example, if one or more implants have been implanted into or removed from the patient anatomy during one or more steps of a surgical procedure, then the method 200 may be used to update or reconstruct the 3D model to reflect the implantation or removal of the implants in the 3D model. Updating or reconstructing the 3D model during a surgical procedure may be particularly useful, for example, when the change in the one or more anatomical features prevents or enables a change in one or more planned trajectories to be used in further steps of the surgical procedure.

The method 200 may further be used to confirm or otherwise verify a predicted movement or other change in a patient's anatomy during a surgical procedure. For example, one or more predicted movements or other changes may be calculated or otherwise determined based on a pre-operative surgical plan that comprises a 3D model. The method 200 may then be used to update the 3D model, and the updated model may be compared to the calculated or otherwise determined predicted movements or other changes to confirm or otherwise verify that the actual movements or changes do (or do not) match the predicted movements or other changes. Where the predicted movements or other changes do not match the actual movements or other changes, the surgeon or other operator may update the surgical plan to compensate for the difference between the actual and predicted movements or other changes.

The method 200 may still further be used to add new information to a 3D model. For example, where a 3D model is initially generated using imagery from an imaging device that is best suited for detected hard tissue, the method 200 may be used to update or reconstruct the 3D model using imagery from an imaging device that is better suited for detecting soft tissue. In this manner, a 3D model can be generated or reconstructed that includes information not just about, for example, the bony elements within an anatomical area of interest, but also about soft tissue within the anatomical area of interest.

As discussed in greater detail below, the method 200 may be carried out using more than one imaging device. Some imaging devices (e.g., devices that utilize X-ray imaging) are better suited for obtaining images of hard tissue than soft tissue, while other imaging devices (e.g., ultrasound, optical coherence tomography) are better suited for obtaining images of soft tissue than hard tissue. As a result, a 3D model generated with imagery from only one device or one type of device may lack sufficient or needed information about one or the other of hard tissue or soft tissue. The method 200 may be used to update a 3D model accordingly. For example, where information about hard tissue is needed to update a 3D model, one or more imaging devices that are well-suited for obtaining images of hard tissue may be used; where information about soft tissue is needed to update a 3D model, one or more imaging devices that are well-suited for obtaining images of soft tissue may be used; and where a 3D model needs to be updated with respect to both hard and soft tissue, a combination of imaging devices well-suited for obtaining images of hard tissue and of imaging devices well-suited for obtaining images of soft tissue may be used.

The method 200 comprises receiving a 3D model (which may also be referred to herein as image data or first image data) of a patient anatomy (step 202). The 3D model may be received via a user interface such as the user interface 110 and/or a communication interface such as the communication interface 108 of a computing device such as the computing device 102, and may be stored in a memory such as the memory 106. The 3D model may also be generated by or uploaded to any component of the system 100. The 3D model may be formed from or comprise preoperative image data, including CT or MRI image data.

In some embodiments, the image data comprising the 3D model may be generated by an imaging device such as the imaging device 112, and may be received directly from the imaging device, or indirectly via any other component of the system 100 or a node of a network to which the system 100 is connected. In such embodiments, the image data may be received via, for example, a communication interface such as the communication interface 108. The image data may already be registered to a patient coordinate system, a robotic coordinate system used by a robot such as the robot 130, and/or a navigation coordinate system used by a navigation system such as the navigation system 114. In other embodiments, the image data may be registered to a patient coordinate system, a robotic coordinate system, and/or a navigation coordinate system after the step 202. The updating or reconstruction of the 3D model according to the method 200 may be accomplished so as to avoid a need for re-registration of the 3D model.

The method 200 also comprises calculating one or more poses for the imaging device to image an anatomical feature (step 204). The calculating may use one or more algorithms such as the pose algorithm 122. The one or more poses may include coordinates for and/or an orientation of the imaging device. In some embodiments, the pose algorithm is configured to calculate the one or more poses based at least in part on the 3D model (e.g., of the patient anatomy). For example, the one or more poses may be calculated based on whether more information is needed about an anatomical feature (or an aspect of an anatomical feature) in the 3D model. For example, if the 3D model comprises one or more artifacts, the poses may be calculated to obtain additional image data needed to remove the one or more artifacts. In other examples, the one or more poses may be calculated based on missing information (e.g., image data, anatomical feature properties) in the 3D model.

In some embodiments, the pose algorithm may be configured to calculate the one or more poses based on at least five degrees of freedom of movement of a robotic arm (e.g., the robotic arm 132) holding the imaging device. In other embodiments, the one or more poses may be based on less than or greater than five degrees of freedom of movement of the robotic arm. In some embodiments, the one or more poses is based on at least six degrees of freedom of movement of the robotic arm holding the imaging device. Such calculations based on multiple degrees of freedom of movement advantageously enable calculations of precise poses in planes and/or focal points that may not be obtainable without the use of a robotic arm.

In other embodiments, the pose algorithm may be configured to calculate the one or more poses based on one or more characteristics of the imaging device (e.g., resolution, image type, image dimension, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more poses may be calculated that will ensure the area of interest is not in a "shadow" of the bony tissue. Also, in embodiments where the poses are calculated based at least in part on the 3D model received in the step 202, the 3D model may be utilized to enable calculation of poses that will enable needed information to be obtained in a more efficient manner than might otherwise be possible.

In some embodiments, the 3D model may comprise one or more artifacts, including but not limited to shadows caused by bony tissue as described above. The one or more poses may be calculated to obtain image data needed to update the 3D model and allow such artifacts to be eliminated from the 3D model, either entirely or in an area of interest.

In yet other embodiments, the pose algorithm may be configured to calculate the one or more poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method 200 also comprises receiving an image from the imaging device at each of the one or more poses to yield an image set for the anatomical feature (step 206). In some embodiments, the image is received directly from the imaging device. In other embodiments, the image is received from or via a memory such as the memory 116, a database, the cloud or another network, or any other source or element. The images in the image set may be or comprise second images, in the sense that the images may comprise updated information about the imaged anatomical feature relative to previously obtained image data (e.g., the 3D model). The method 200 may include causing the imaging device (which, as noted above, may be for example an imaging device 112) to be automatically positioned and/or automatically actuated to obtain the image. For example, the imaging device may be automatically positioned at one of the poses calculated at the step 204 by a robotic arm such as the robotic arm 132. In embodiments where the imaging device includes two or more imaging devices, one robotic arm may position each imaging device or two or more robotic arms may each hold a different imaging device. For example, in some embodiments, a first imaging device is held by a first robotic arm and a second imaging device is held by a second robotic arm. In some embodiments, the imaging device comprises a plurality of imaging devices and at least one arm of a plurality of robotic arms is configured to selectively hold each of the plurality of imaging devices. In other embodiments, the at least one arm of the plurality of robotic arms may configured to move the imaging device, in sequence, to the one or more poses. In other embodiments, a first arm is configured to position a first imaging device independently of a second arm positioning a surgical tool or a second imaging device. In other examples, the imaging device may be positioned by a surgeon assisted by a navigation system such as the navigation system 114. For example, the surgeon may reference a display of or otherwise utilize the navigation system to position an imaging device in one of the one or more imaging devices poses calculated in the step 204.

The image set may comprise one or more 2D images, one or more 3D images, or a combination of one or more 2D images and one or more 3D images. In some embodiments, one imaging device may be used to obtain the image set. In other embodiments, multiple imaging devices may be used to obtain the image set. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In other embodiments, a first imaging device may obtain an image at each pose of a first set of the one or more poses and a second imaging device may obtain another image at each pose of a second set of the one or more poses.

In some embodiments, as previously described, the imaging device may be an ultrasound probe, and may comprise a detector or receiver of the ultrasound probe held by a first robotic arm and an emitter or transducer of the ultrasound probe held a known distance from and opposite the detector or receiver by a second robotic arm having at least five degrees of freedom of movement. In the same embodiments, the one or more poses for the imaging device includes one or more poses for both the emitter or transducer and the detector or receiver. In other words, references to a pose of an imaging device, where the imaging device is a probe comprising an emitter or transducer and a detector or receiver, include a pose (e.g., a position and orientation) of the emitter or transducer and a pose of the detector or receiver. The one or more poses may be poses in which both the emitter or transducer and the detector or receiver are positioned in contact with a patient, to provide an air-free (or substantially air-free) path between the emitter or transducer and the detector or receiver. A time of flight may be determined by measuring the time that elapses between output of an ultrasonic signal from the emitter or transducer and receipt of the ultrasonic signal by the detector or receiver. Such information (e.g., the time of flight) may beneficially provide additional information for inclusion in the 3D model, as described below. In other embodiments, the imaging device may include more than one imaging device and each imaging device may be a different type of imaging device. For example, in some embodiments, a first imaging device may be an ultrasound probe and a second imaging device may be an optical coherence tomography (OCT) camera. The OCT camera may advantageously image a first depth of a patient at high resolution for viewing anatomical features (e.g., vessels, nerves, and/or tumors) not visible or not easily viewable in other image modalities. The ultrasound probe may advantageously image a second depth greater than the first depth of the patient to obtain more information about anatomical features of the patient. Further, in some embodiments, an OCT camera and an ultrasound probe may be used together, and each held by a separate robotic arm, as imaging from the OCT camera and the ultrasound probe advantageously do not interfere with each other.

The method 200 further comprises updating (e.g., reconstructing) a representation of the anatomical feature in the 3D model of the patient anatomy to yield an updated 3D model of the patient anatomy (step 208). The updating or reconstruction may be based on at least one image from the image set and the pose corresponding to the at least one image. The 3D model may be updated using one or more algorithms such as the model update or comparison algorithm 128. In some embodiments, updating the 3D model may occur after a step of a surgical procedure, prior to a step of a surgical procedure, or during a step of a surgical procedure.

Various attributes of the 3D model may be updated or improved including, but not limited to, model resolution, model depth, information about an anatomical feature, etc. For example, images from an ultrasound probe and/or time of flight may provide properties of tissue (e.g., stiffness of tissue, hardness of tissue, thermal, fluid, electromagnetic, acoustic, and/or magnetic resonance properties). In another example, images from an OCT camera may provide high resolution imaging to provide detailed information about an anatomical feature (e.g., a nerve, tissue, artery, or veins). In some embodiments, updating the representation of the anatomical feature in the 3D model of the patient anatomy comprises adding soft tissue data from the image data set to the 3D model of the patient anatomy (which may comprise hard and/or soft tissue data). In some embodiments, the soft tissue data (e.g., the image data set) may be obtained from an OCT camera.

Updating the 3D model may comprise using the pose(s) corresponding to the at least one image to identify a portion of the 3D model that corresponds to the at least one image. For example, the content of the at least one image may be matched or otherwise correlated (e.g., using a known position and orientation from which the at least one image was taken) to a portion of the 3D model and the portion of the 3D model may be updated or replaced based on the at least one image. Stated differently, because the precise pose corresponding to each image is known, the 3D model may be updated based on each image without needing to include any fiducials or other markers in each image. As such, positional knowledge of the image from the image set advantageously allows for precise updating of the 3D model.

After the 3D model is updated, one or more of the steps 202-208 may be repeated until the 3D model is fully updated (e.g., in advance of a surgical step in a surgical procedure, or after such a surgical step) and meets a predetermined threshold and/or is approved by a surgeon or operator. During a surgical operation, if the 3D model requires further updating due to a shift or movement in the patient anatomy, the steps 206 to 208 (or any of the steps 202-208) may be repeated, and/or the 3D model may be further updated or reconstructed as described below with respect to FIG. 3. Such repetition of the steps may result in updating or reconstructing the entire 3D model or a localized portion of the 3D model, thereby providing increased accuracy of the 3D model throughout the operation.

Figure 3:
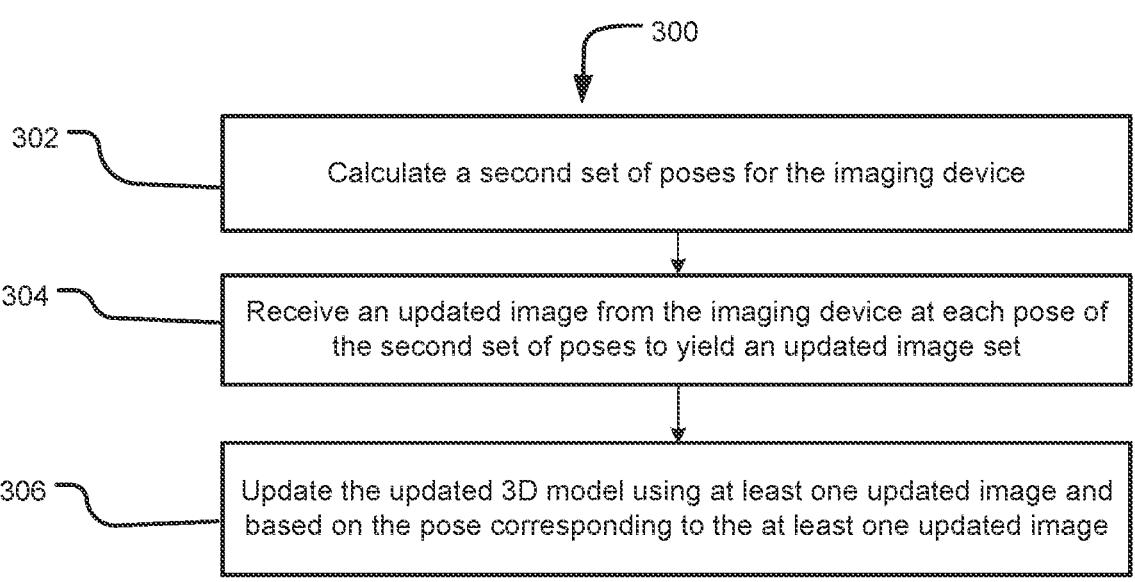
FIG. 3 is another flowchart of a method according to at least one embodiment of the present disclosure.

Turning now to FIG. 3, a method 300 for updating an updated 3D model according to embodiments of the present disclosure may be executed, for example, in whole or in part, on a computing device such as the computing device 102 or similar device, and may utilize one or more other components of the system 100 or similar components. One or more aspects of the method 300 may be carried out or otherwise occur when an updated 3D model (such as that resulting from the method 200) requires updating after movement in the patient anatomy has occurred or is suspected to have occurred. The steps 302-306 of the method 300 generally correspond to the steps 204-208 of the method 200, except that the steps 302-306 of the method 300 are described in connection with updating a 3D model that has already been updated (e.g., in accordance with the method 200) at least once. The method 300 may be used in conjunction with the method 200 (or separately), for example, in each of the use cases described above with respect to the method 200.

The method 300 comprises calculating a second set of poses for an imaging device (e.g., the imaging device 112) (step 302). The second set of poses is calculated after a first set of poses is calculated, and may be calculated according to, for example, step 204. The calculating may use one or more algorithms such as the pose algorithm 122. The second set of poses may include coordinates for and/or an orientation of the imaging device. At least one pose of the second set of poses may match at least one pose of the first set of poses. In other embodiments, none of the set of second poses matches the set of first poses.

In some embodiments, the pose algorithm is configured to calculate the one or more poses based at least in part on the updated 3D model. The second set of poses may be calculated to position the imaging device to image a specific, localized portion of the patient anatomy to update a portion of the updated 3D model, thereby reducing imaging and overall operating time. Thus, for example, if a specific anatomical feature of a patient has shifted or is suspected to have shifted, the second set of poses may be calculated to obtain images of only that anatomical feature (or a portion thereof). Similarly, the pose algorithm may be configured to calculate the second set of poses based on input or feedback from the surgeon or operator. For example, the surgeon or operator may wish to obtain an updated image of an anatomical feature from a certain angle or plurality of angles.

The method 300 also comprises receiving an updated image from the imaging device at each pose of the second set of poses to yield an updated image set (step 304). In some embodiments, the updated image is received directly from the imaging device. In other embodiments, the updated image is received from or via a memory such as the memory 116, a database, the cloud or another network, or any other source or element. The method 300 may include causing the imaging device (which, as noted above, may be, for example, an imaging device 112) to be automatically positioned and/or automatically actuated to obtain the updated image. For example, the imaging device may be automatically positioned at one pose of the second set of poses calculated at the step 302 by a robotic arm, such as the robotic arm 132. In other examples, the imaging device may be positioned by a surgeon assisted by a navigation system, such as the navigation system 114. For example, the surgeon may reference a display of or otherwise utilize the navigation system to position an imaging device in one of the one or more updated imaging device poses calculated in the step 302.

Similar to step 206 as described above, the updated image set may comprise 2D images, 3D images, or a combination of 2D images and 3D images. In some embodiments, one imaging device may be used to obtain the updated image set. In other embodiments, multiple imaging devices may be used to obtain the updated image set. For example, a first imaging device may obtain a first one of the updated images independently of a second imaging device obtaining a second one of the updated images. In some embodiments, the imaging device is a first imaging device, the robotic arm is a first robotic arm, and the first imaging device obtains a first one of the updated images independently of a second imaging device held by a second robotic arm obtaining a second one of the updated images. In other embodiments, one imaging device may be used to obtain the updated image set. In another example, at least a first one of the updated images may be obtained with a first imaging device held by a robotic arm in a corresponding first pose of the second set of poses and at least a second one of the updated images may be obtained with a second imaging device held by the robotic arm in a corresponding second pose of the second set of poses.

The method 300 further comprises updating or reconstructing the updated 3D model of the patient anatomy using at least one updated image from the updated image set and based on the pose of the second set of poses corresponding to the at least one updated image (step 306). The updated 3D model may be updated or reconstructed using one or more algorithms such as the model update or comparison algorithm 128. Similar to step 208 as described above, updating the updated 3D model may occur after a step of a surgical procedure, prior to a step of a surgical procedure, or during a step of a surgical procedure. Updating the updated 3D model may also occur when the updated 3D model is determined to be missing information (e.g., soft tissue data, information about an anatomic element, hard tissue data, etc.). For example, the patient anatomy may shift, or one or more anatomical details may be determined to be missing from the updated 3D model. In such instances, updating the updated 3D model enables the missing anatomical details to be added to the updated 3D model.

The method 300 may also comprise comparing at least one updated image from the updated image set (of the method 300) with at least one image of the image set (which may be obtained using the method 200) to identify and/or verify movement of an anatomical feature depicted in the at least one image. The method 300 may further comprise determining at least one of a position and/or an orientation of the anatomical feature based at least in part on one or more updated images of the updated image set. Such information (i.e., the position and/or orientation) may be used to calculate and optimize new paths or positions and orientations for surgical tools. Updating the 3D model as needed using method 300 beneficially increases accuracy of the 3D model during operation in real-time.

Turning now to FIG. 4, a method 400 for model registration according to embodiments of the present disclosure may be executed, for example, in whole or in part, on a computing device such as the computing device 102 or similar device, and may utilize one or more other components of the system 100 or similar components. One or more aspects of the method 400 may be performed by or with a surgical robot, a surgeon, or a combination of both using one or more imaging devices such as the imaging device 112.

The method 400 may be used, for example, to register a 3D model to a robot space. Where a robot (e.g., the robot 130) is affixed to a patient, the method 400 may also be used to register a 3D model to a patient space. Such registration is possible because the images taken as part of the method 400 are taken from known poses (e.g., because they are taken with imaging devices held by a robotic arm of a robot such that the precise position and orientation of the imaging device is known). Images obtained pursuant to the method 400 may also be taken with imaging devices tracked by a navigation system such that the position and orientation of the imaging device relative to a navigation space is known. Where the navigation space is registered to, for example, a 3D model or other pre-operative image space, and/or to a robotic space, the images taken from known poses relative to the navigation space may be registered to the robotic space and/or to the 3D model or other pre-operative image space.

Pre-operative 3D models may be generated, for example, from CT or MRI images. As described in greater detail below, particular shapes may be identified in images taken according to the method 400 and matched with the same shapes in the 3D model. Because the position and orientation from which each image taken pursuant to the method 400 is known, the matching of shapes in the images with the same shapes in the 3D model enables the model space to be registered to the robotic space (where the imaging device(s) used to obtain the images is/are held by a robotic arm of a robot) or to a navigation space (where a position and orientation of the imaging device(s) used to obtain the images is/are tracked by a navigation system). Where the robotic space and/or the navigation space is already linked or otherwise registered to a patient space (e.g., in the case of a robot, where the robot is fixedly attached to the patient), the model space may be registered to the patient space.

The method 400 may also be used to confirm an existing registration intraoperatively. For example, where a model space has been pre-operatively registered to a robotic space, a navigation space, and/or a patient space prior to a surgical procedure, the method 400 may be utilized to obtain pre-operative images of one or more anatomical features of the patient from known positions and orientations (e.g., while the pre-operative registration is known to be valid). Then, during the surgery (e.g., after a surgical step that may have caused movement of one or more anatomical features of the patient, or prior to a surgical step for which accuracy of the registration is critical), an additional set of images may be taken from the same poses as the pre-operative images and compared to the pre-operative images. If the images are identical (or otherwise show an identical relationship between or among the imaged anatomical features), the pre-operative registration may be confirmed. On the other hand, if the comparison reveals that one or more anatomical features has/have shifted from a preoperative position/orientation thereof, then the surgeon or other operator can determine whether re-registration is needed. In some embodiments, such as where a robot (e.g., the robot 130) is completing a surgical procedure autonomously, the robot may itself determine whether re-registration is needed, based on one or more predetermined criteria (such as, for example, the extent of the movement of the one or more anatomical features).

Where re-registration is needed, the method 400 may be used to complete the re-registration. Such re-registration may be limited to a local area or volume (e.g., where the surgical process has changed one or more anatomical features in a way that necessitates re-registration), or the re-registration may be needed over the entire area or volume of the previous registration.

The ability to easily complete intraoperative re-registration not only reduces the time, cost, and complexity of surgical procedures, but also enables potential changes to the surgical procedure workflow to enhance efficiency. For example, while now surgeons may structure each step of a surgical procedure so as to avoid doing anything that might necessitate intraoperative re-registration (because of the time and complexity of other registration procedures), the present disclosure significantly reduces if not eliminates that time and complexity, such that surgical procedures may be planned without regard for whether intraoperative re-registration will be needed.

The method 400 comprises receiving a first image, or a 3D model, of an anatomical portion of a patient (step 402). The first image may be a 2D or 3D image or a set of 2D and/or 3D images. The first image or 3D model may be received via a user interface such as the user interface 110 and/or a communication interface such as the communication interface 108 of a computing device such as the computing device 102, and may be stored in a memory such as the memory 106. The first image or 3D model may also be generated by or uploaded to any component of the system 100. The first image or 3D model may be preoperative image data or image data taken during a registration process or prior to operation, including CT or MRI image data.

In some embodiments, the first image or 3D model may be generated by an imaging device such as the imaging device 112 and/or may be received directly from the imaging device, or indirectly via any other component of the system 100 or a node of a network to which the system 100 is connected. The first image or 3D model may already be registered to a patient coordinate system, a robotic coordinate system used by a robot such as the robot 130, and/or a navigation coordinate system used by a navigation system such as the navigation system 114. In other embodiments, the first image or 3D model may be registered to a patient coordinate system, a robotic coordinate system, and/or a navigation coordinate system after the step 402.

The method 400 also comprises calculating one or more poses of the imaging device based on the first image or 3D model (step 404). The calculating may use one or more algorithms such as the pose algorithm 122. The one or more poses (also referred to as a recording sequence) may be or include coordinates for and/or an orientation for an imaging device such as the imaging device 112. In some embodiments, each pose may be a pose of a robotic arm that holds or will hold an imaging device such as the imaging device 112. The imaging device may advantageously not emit ionizing radiation, thereby providing an imaging device that can be used multiple times without emitting harmful radiation. In some embodiments, the imaging device may be, but is not limited to, an ultrasound probe and/or an OCT camera. In the embodiments where the imaging device is an ultrasound probe, a detector or receiver of the ultrasound probe may be held by a first robotic arm and an emitter or transducer of the ultrasound probe may be held a known distance from and opposite the detector or receiver by a second robotic arm having at least five degrees of freedom of movement. In the same embodiments, the one or more poses for the imaging device may include one or more poses for both the emitter or transducer and the detector or receiver. The one or more poses may be poses in which both the emitter or transducer and the detector or receiver are positioned in contact with a patient, to provide an air-free (or substantially air-free) path between the emitter or transducer and the detector or receiver. A time of flight may be determined by measuring the time that elapses between output of an ultrasonic signal from the emitter or transducer and receipt of the ultrasonic signal by the detector or receiver.

In some embodiments, the pose algorithm may take into account a change in position of the patient from a first position in which the first image or 3D model was taken or constructed from and a second position in which the patient will be during a surgical procedure. For example, the first image or 3D model may have been obtained with the patient in a supine position, and a planned operation may require the patient to be in a prone position. The pose algorithm may calculate poses based in part on this switch in patient position. In some embodiments, the one or more poses may be calculated relative to a position of the patient such that the one or more calculated poses may be utilized with the patient in different positions and orientations.

In some embodiments, the pose algorithm may be configured to calculate the one or more poses based on at least five degrees of freedom of movement of a robotic arm (e.g., the robotic arm 132) holding the imaging device. In other embodiments, the one or more poses may be based on less than or greater than five degrees of freedom of movement of the robotic arm. In some embodiments, the one or more poses is based on at least six degrees of freedom of movement of the robotic arm holding the imaging device. Such calculations based on multiple degrees of freedom of movement advantageously enables calculations of precise poses in planes and/or focal points that may not be obtainable by imaging devices without a robotic arm.

In other embodiments, the pose algorithm (e.g., the pose algorithm 122) is configured to calculate the one or more poses based on one or more characteristics of the imaging device (e.g., resolution, image type, image dimension, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more poses may be calculated that will ensure the area of interest is not in a "shadow" of the bony tissue. Also, in embodiments where the poses are calculated based at least in part on the first image or 3D model received in the step 402, the first image or 3D model may be utilized to enable calculation of poses that will enable needed information to be obtained in a more efficient manner than might otherwise be possible.

In some embodiments, the first image or 3D model may comprise one or more artifacts, including but not limited to shadows caused by bony tissue as described above. The one or more poses may be calculated to obtain image data needed to update the first image or 3D model and allow such artifacts to be eliminated from the first image or 3D model, either entirely or in an area of interest.

In yet other embodiments, the pose algorithm may be configured to calculate the one or more poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method 400 also comprises receiving an image from the imaging device at each of the one or more poses to yield an image set (step 406). In some embodiments, the image is received directly from the imaging device. In other embodiments, the image is received from or via a memory such as the memory 116, a database, the cloud or another network, or any other source or element. The images in the image set may be or comprise second images, in the sense that the images may comprise updated information about the imaged anatomical feature relative to the first image or 3D model. The second images may each depict at least one anatomical feature of the patient. The second images may be obtained from an imaging device using an imaging modality different from an imaging modality of an imaging device used to obtain the first image or 3D model. For example, in some embodiments, the first image or 3D model is created with a first image modality and the imaging device for obtaining the images for the image set is a second image modality different than the first image modality.

The method 400 may include causing the imaging device (which may be, for example, an imaging device 112) to be automatically positioned, oriented, and/or automatically actuated to obtain the image. For example, the imaging device may be automatically positioned by a robotic arm, such as the robotic arm 132. In other examples, the imaging device may be positioned by a surgeon assisted by a navigation system such as the navigation system 114.

The image set may comprise one or more 2D images, one or more 3D images, or a combination of one or more 2D images and one or more 3D images. Each second image may depict an anatomical feature of the patient. In some embodiments, one imaging device may be used to obtain the image set. In other embodiments, multiple imaging devices may be used to obtain the image set. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In other embodiments, a first imaging device may obtain an image at each pose of a first set of the one or more poses and a second imaging device may obtain another image at each pose of a second set of the one or more poses.

In some embodiments, a plurality of robotic arms is configured to selectively hold a plurality of imaging devices. In other words, multiple robotic arms can each hold an imaging device. Each robotic arm may also be configured to move an imaging device being held by the robotic arm, in sequence, to the one or more poses. In some embodiments, at least one of the second images is obtained with a first imaging device held by the first arm in one of the one or more poses and at least another one of the second images is obtained with a second imaging device held by the first arm or a second arm in another one of the one or more poses. In other embodiments, a first arm is configured to position a first imaging device independently of a second arm positioning a surgical tool or a second imaging device.

The method 400 further comprises aligning the at least one anatomical feature in each second image with a corresponding anatomical feature in the first image or 3D model (step 408). One or more algorithms such as the image update or comparison algorithm 126 may be used for the aligning. The aligning may be based at least in part on the corresponding one or more poses. For example, a position of one or more anatomical features in each second image may be calculated based on the known position and/or orientation of the imaging device when each second image was taken, and matched to a position of one or more anatomical features in the first image or 3D model (calculated based on the known position and/or orientation of the imaging device when each first image or 3D model was taken) and the second images may be compared to determine if the one or more anatomical features are present therein. In other examples, feature recognition may be used to identify a feature of an anatomical feature in each of the second image and the first image or 3D model, based upon which the first image or 3D model and the images may be matched to each other. For example, a contour of a vertebrae may be identified in the first image or 3D model and the corresponding second image, and the corresponding second image may be matched to the first image or 3D model at or using the identified contour. In other examples, the alignment may use artificial intelligence, machine learning, or pose information. When the alignment is complete, the alignment provides a relative orientation and a relative position of the anatomical feature in the second image to the first image or 3D model.

The method 400 further comprises registering an image space to a patient space based on the alignment (step 410). The registering may utilize a registration algorithm such as the registration algorithm 124. The alignment enables mapping of the first image or 3D model to the second image space and from the second image space to the patient space, and thus enables a determination of the relative positions and/or orientations of the patient's anatomical features between a first orientation of the patient (e.g., when the 3D model was taken) and a second orientation of the patient (e.g., when the set of second images were taken). Registering the image space to the patient space advantageously occurs without a fiducial marker, thereby reducing not just the number of components needed in the surgical space to accomplish the registration, but also reducing the complexity of the registration process as well as the time required to complete the registration process.

The method 400 may further comprise verifying the registration by evaluating the alignment, and determining that the registration is invalid when the alignment reveals a discrepancy between an imaged position of an anatomical feature and a position of the anatomical feature in the first image or 3D model. For example, the registration may be determined to be invalid when the anatomical feature in the imaged position is different from a position of the anatomical feature in the first image or 3D model. Conversely, the registration may be determined to be valid when the anatomical feature in the imaged position is the same as a position of the anatomical feature in the first image or 3D model.

The method 400 may further comprise receiving an updated image from the imaging device at at least one of the one or more poses to yield a second image set. In some embodiments, the updated image is received directly from the imaging device. In other embodiments, the updated image is received from or via a memory such as the memory 116, a database, the cloud or another network, or any other source or element. The method may also further comprise comparing each updated image in the second image set to a corresponding image from the image set (e.g., a first image set of step 406) to determine movement of the anatomical feature. The updated image is obtained after the last image of the first image set is taken. The updated image may be obtained prior to a surgical step, during a surgical step, or after a surgical step. The method 400 may further comprise reregistering the image space to the patient space based on the second image set.

One or more of the steps 402-410 may be repeated when an anatomical feature has moved or is suspected to have moved or during the initial registration step when registration ambiguities are identified that prevent a valid registration from occurring. Repetition of the steps 404-410 (or any of steps 402-410) may be performed and/or the first image or 3D model may be further updated.

Turning now to FIG. 5, a method 500 for registration verification according to embodiments of the present disclosure may be executed, for example, in whole or in part, on a computing device such as the computing device 102 or similar device, and may utilize one or more other components of the system 100 or similar components. One or more aspects of the method 500 may be performed by or with a surgical robot, a surgeon, or a combination of both using one or more imaging devices, such as the imaging device 112. The method 500 may be used, for example, in connection with each of the use cases described above with respect to the method 400.

The method 500 comprises calculating one or more first poses for an imaging device (step 502). The calculating may utilize a pose algorithm such as the pose algorithm 122. The one or more poses may be or include coordinates for and/or an orientation of the imaging device.

In some embodiments, the calculating the one or more first poses is based at least in part on information about the patient's anatomy. In some embodiments, the calculating the one or more first poses is based on a surgical plan or preoperative image. In other embodiments, the algorithm may be configured to calculate the one or more first poses based on one or more characteristics of the imaging device (e.g., resolution, image type, image dimension, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more first poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more poses may be calculated that will ensure the area of interest is not in a "shadow" of the bony tissue.

In some embodiments, the pose algorithm may be configured to calculate the one or more first poses based on at least five degrees of freedom of movement of a robotic arm (e.g., the robotic arm 132) holding the imaging device. In other embodiments, the one or more first poses may be based on less than or greater than five degrees of freedom of movement of the robotic arm. In some embodiments, the one or more first poses is based on at least six degrees of freedom of movement of the robotic arm holding the imaging device. Such calculations based on multiple degrees of freedom of movement advantageously enables calculations of precise poses in planes and/or focal points that may not be obtainable by imaging devices without a robotic arm.

In yet other embodiments, the pose algorithm may be configured to calculate the one or more first poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method 500 also comprises calculating one or more second poses (step 504). The calculating may utilize a pose algorithm such as the pose algorithm 122. Similarly to step 502 as described above, the one or more second poses may be or include coordinates for and/or an orientation of the imaging device. The one or more second poses may be the same as the one or more first poses. In other embodiments, at least one of the one or more second poses may be the same as the one or more first poses. In yet other embodiments, none of the one or more second poses are the same as the one or more first poses.

In some embodiments, the pose algorithm may be configured to calculate the one or more second poses based on at least five degrees of freedom of movement of a robotic arm (e.g., the robotic arm 132) holding the imaging device. In other embodiments, the one or more second poses may be based on less than or greater than five degrees of freedom of movement of the robotic arm. In some embodiments, the one or more second poses are based on at least six degrees of freedom of movement of the robotic arm holding the imaging device. Such calculations based on multiple degrees of freedom of movement advantageously enables calculations of precise poses in planes and/or focal points that may not be obtainable by imaging devices without a robotic arm.

In some embodiments, the calculating the one or more second poses is based at least in part on information about the patient's anatomy. In some embodiments, the calculating the one or more second poses is based on a surgical plan or preoperative image. In other embodiments, the algorithm may be configured to calculate the one or more second poses based on one or more characteristics of the imaging device (e.g., resolution, image type, image dimension, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more second poses may be calculated that will ensure the area of interest is not in a "shadow" of the bony tissue.

In yet other embodiments, the pose algorithm may be configured to calculate the one or more second poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method 500 also comprises receiving a first image from the imaging device, during a first time period, at each of the one or more first poses to yield a first image set (step 506). In some embodiments, the first image is received directly from the imaging device. In other embodiments, the first image is received from or via a memory such as the memory 116, a database, the cloud or another network, or any other source or element. Each first image of the first image set may depict at least one anatomical feature. The method 500 may include causing the imaging device (which, as noted above, may be for example an imaging device 112) to be automatically positioned and/or automatically actuated to obtain the image. For example, the imaging device may be automatically positioned at one of the first poses calculated at the step 502 by a robotic arm such as the robotic arm 132. In other examples, the imaging device may be positioned by a surgeon assisted by a navigation system such as the navigation system 114. For example, the surgeon may reference a display of or otherwise utilize the navigation system to position an imaging device in one of the one or more first imaging devices poses calculated in the step 502.

The first image set may comprise one or more 2D images, one or more 3D images, or a combination of one or more 2D images and one or more 3D images. In some embodiments, one imaging device may be used to obtain the first image set. In other embodiments, multiple imaging devices may be used to obtain the first image set. For example, a first imaging device may obtain a first one of the first images independently of a second imaging device obtaining a second one of the first images. In another example, at least a first one of the first images may be obtained with a first imaging device held by a robotic arm in a corresponding first one of the first poses and at least a second one of the first images may be obtained with a second imaging device held by the robotic arm in a corresponding second one of the first poses.

The method 500 further comprises receiving a second image from the imaging device, during a second time period after the first time period, at each of the one or more second poses to yield a second image set (step 508). In some embodiments, the second image is received directly from the imaging device. In other embodiments, the second image is received from an operator of the imaging device via the user interface. Each second image of the second image set may depict at least one anatomical feature. The second time period may correspond to a time period prior to a surgical step, during a surgical step, or after a surgical step.

The method 500 may include causing the imaging device to be automatically positioned and/or automatically actuated to obtain the second image. For example, the imaging device may be automatically positioned at one of the second poses calculated at the step 504 by a robotic arm such as the robotic arm 132. In other examples, the imaging device may be positioned by a surgeon assisted by a navigation system such as the navigation system 114. For example, the surgeon may reference a display of or otherwise utilize the navigation system to position an imaging device in one of the one or more second imaging devices poses calculated in the step 504.

The second image set may comprise one or more 2D images, one or more 3D images, or a combination of one or more 2D images and one or more 3D images. In some embodiments, one imaging device may be used to obtain the second image set. In other embodiments, multiple imaging devices may be used to obtain the second image set. For example, a first imaging device may obtain a first one of the second images independently of a second imaging device obtaining a second one of the second images. In another example, at least a first one of the second images may be obtained with a first imaging device held by a robotic arm in a corresponding first one of the second poses and at least a second one of the second images may be obtained with a second imaging device held by the robotic arm in a corresponding second one of the second poses.

The method 500 further comprises comparing the first image set to the second image set to verify a registration of robot space to patient space (step 510). In some examples, the comparison may include determining, based on the first image set and the second image set, whether an anatomical feature depicted in one or more of the first images and in one or more of the second images remained in the same position from the first time period to the second time period. Determining a change in the position of the anatomical feature may comprise using feature recognition (whether alone or in conjunction with pose information about a pose of the imaging device when each image was taken) to match the anatomical feature in each second image to the anatomical feature in each corresponding first image in some embodiments. In other embodiments, artificial intelligence, machine learning, and/or pose information may be used to determine a change in the position of the anatomical feature. A registration of robot space to patient space may be verified when a position of one or more anatomical features in each of the second images matches the position of the one or more anatomical features in each corresponding first image. Alternatively, a change is detected when a position of an anatomical feature in one of the second images does not match a position of the anatomical feature in a corresponding first image. If a change is detected, re-registration or a localized re-registration may be necessary, and may be completed, for example, using one or more steps of the method 400. A localized reregistration may comprise determining an updated position of the anatomical feature based on the detected change (and/or based on information about the first poses and/or the second poses) and updating the registration based on the updated position.

Figure 6:
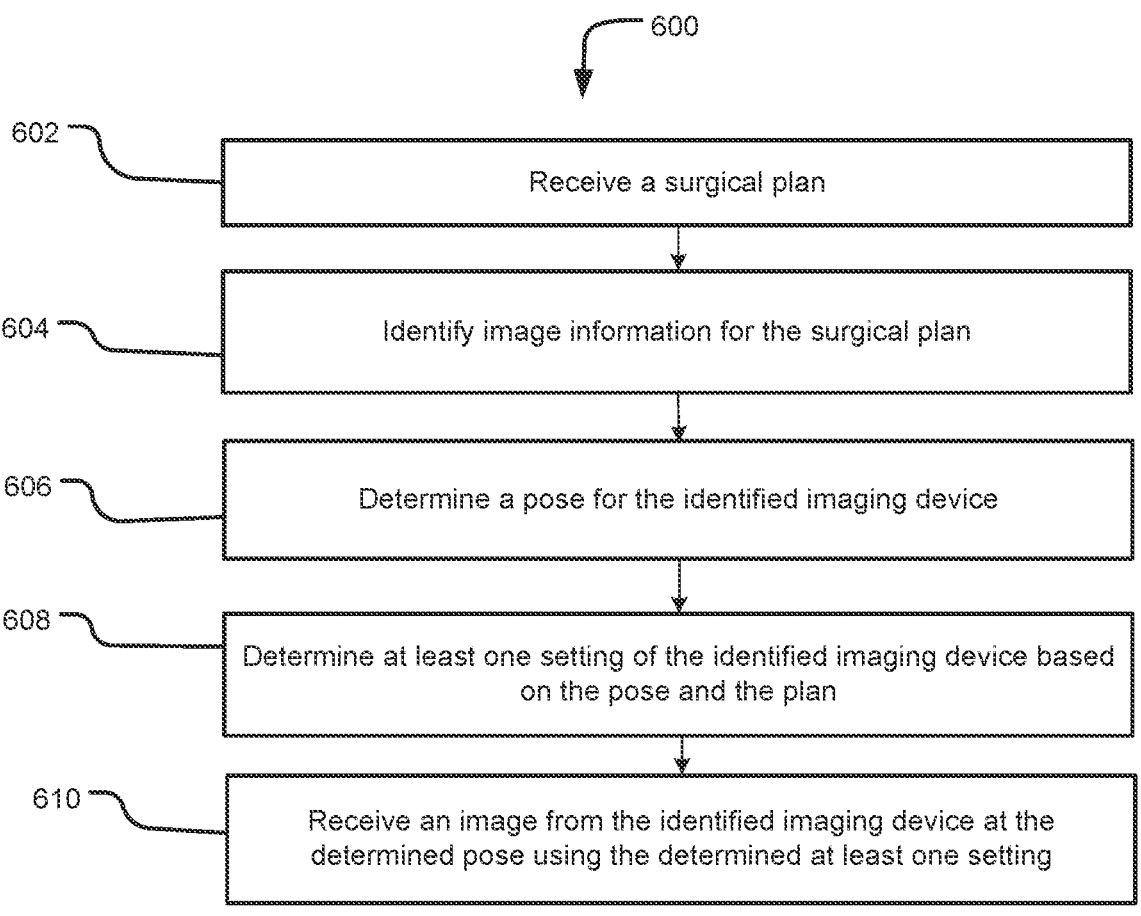
FIG. 6 is a further flowchart of a method according to at least one embodiment of the present disclosure.

Turning now to FIG. 6, a method 600 for obtaining images based on a surgical plan such as the surgical plan 134 according to embodiments of the present disclosure may be executed, for example, in whole or in part, on a computing device such as the computing device 102 or a similar device, and may utilize one or more components of the system 100 or similar components. One or more aspects of the method 600 may be performed by or with a surgical robot, a surgeon, or a combination of both using one or more imaging devices such as the imaging device 112.

The method 600 may be used, for example, to improve or optimize the settings of one or more imaging devices (such as, for example, an imaging device 112) prior to the use thereof to obtain one or more images, to increase the likelihood of obtaining useable images that have the desired information therein and to reduce the time needed to obtain such images. Currently, for example, a surgeon or other operator may need to take time to review a surgical plan, identify a needed image, determine which imaging device to use to obtain the needed image, review the settings of the imaging device, adjust those settings as necessary, take a trial image, re-adjust the settings to make any needed corrections, and then take one or more additional images. According to embodiments of the present disclosure, a processor (such as, for example, the processor 104) may analyze a surgical plan, identify information that needs to be gathered by obtaining one or more images of the relevant anatomical area, determine which of a plurality of imaging devices is best suited for obtaining the needed images, determine which settings of the selected imaging device(s) are needed to obtain the needed information, and then cause a robotic arm to automatically position the imaging device(s) in one or more appropriate positions and orientations to obtain the needed images—all with little or no input from a surgeon or other operator.

The method 600 may also be used, for example, to combine images from different imaging devices using the known positions and orientations of each imaging device. For example, images from an ultrasound device may be combined with images from an OCT camera based on the known positions and orientations of the ultrasound device and the OCT camera when each image is taken.

The method 600 may also be used, for example, for providing doppler imaging in which a first layer of image data may be portrayed on top of a second layer of image data. The first layer and the second layer may be different types of image data. For example, second layer of image data may be X-ray image data and the first layer of image data may be ultrasonic image data. In such examples, soft tissue (e.g., a flow of blood within a heart or vessels) may be displayed on top of hard tissue (e.g., bone). Such doppler imaging may be used to detect velocity changes of various elements. It will be appreciated that any number or type of image data layer may be portrayed on top of any number or type of image data.

The method 600 may also be used, for example, to eliminate artifacts from, or to reduce the number of artifacts in, a preoperative model or other imagery. A processor such as the processor 104 may be utilized to identify such artifacts (or to receive an input from a surgeon or other operator that identifies such artifacts), determine what additional information is needed to eliminate the artifacts from the preoperative model or other imagery, select one or more imaging devices to use to obtain the additional information, identify one or more needed settings of the selected imaging device, configure the imaging device to reflect the needed settings, calculate one or more poses at which to position the imaging device to obtain the needed images, and then cause the imaging device to obtain one or more images at the one or more poses (e.g., by controlling a robotic arm holding the imaging device to move the imaging device to the calculated pose, and by causing the imaging device to obtain an image once the imaging device has reached the calculated pose).

The method 600 comprises receiving a surgical plan (step 602). The surgical plan, which may be, for example, the same as or similar to the surgical plan 134, may be received via a user interface such as the user interface 110 and/or a communication interface such as the communication interface 108 of a computing device such as the computing device 102, and may be stored in a memory such as the memory 106 of the computing device. The surgical plan may also be generated by or uploaded to any component of the system 100. The surgical plan may include information about one or more planned movements of a robotic arm such as the robotic arm 132 to position an imaging device (e.g., the imaging device 112) during a surgical procedure in the pose. The information may also include a timeline or schedule of the one or more planned movements. The one or more planned movements may be or include one or more of timestamps, a type of movement (e.g., translational and/or rotational), a duration of the movement, and/or positional information (e.g., coordinates, orientation). The surgical plan may include information about one or more artifacts that may obscure or otherwise interfere with obtaining an image.

The surgical plan, in some embodiments, comprises a 3D model and/or other image data of a patient anatomy. In such embodiments, the image data may be processed using an image processing algorithm such as the imaging processing algorithm 120 to resolve gray level scales for calibrating an imaging device. During calibration, a normalized gray scale value may be applied to the imaging device. Such calibration may occur during maintenance of the imaging device.

The method 600 also comprises identifying image information needed to carry out the surgical plan (step 604). The needed image information may be or include information about one or more anatomical features (including, for example, location (including location relative to one or more other anatomical features), properties and/or types of the one or more anatomical features), and/or required image depth, resolution, and/or type.

The method 600 may also comprise identifying an imaging device needed to obtain the identified image information. The imaging device (which may be, for example, an imaging device 112) may be selected based on the needed image information. For example, the imaging device may be selected based on whether characteristics of the imaging device enable the imaging device to obtain the identified image information. For example, one imaging device (e.g., an OCT camera) may be selected based on a need for detailed images of anatomical features near a surface of the anatomical tissue, and/or because imaging over a long period of time is needed (such that X-ray radiation and/or ultrasonic heating would be a concern if an X-ray imaging device or ultrasonic imaging device, respectively, were used). Another imaging device (e.g., an ultrasound probe) may be selected based on a need for images at a greater depth. The imaging device may also be selected based on dimensions of the imaging device. For example, an imaging device may be selected for its ability to fit through a small incision and/or to be used in a minimally invasive surgical system. In some embodiments, two or more imaging devices (or one imaging device with two or more configurations) may be needed to gather all of the identified imaging information. For example, an ultrasound probe may be used to gather imaging information at greater depths, and an OCT device may be used to gather imaging information at shallower depths. In other embodiments, an OCT device may be used for internal imaging (e.g., of an artery) while an ultrasound probe is used for external imaging.

The method 600 also comprises determining a pose for the imaging device to obtain the identified image information (step 606). The one or more poses may be determined using a pose algorithm such as the pose algorithm 122. The one or more poses may be determined based at least in part on the surgical plan and/or other information about the anatomy to be imaged, so as to determine poses of the imaging device that will provide as much information as possible. This is particularly important, for example, when imaging complex bony structures, such as the spinal vertebrae, which (depending on the imaging device used) may create shadows and thus reduce the amount of information that can be gathered from an image. In embodiments where the surgical plan includes a 3D model, determining the pose may be further based on the 3D model. In such embodiments, the 3D model includes information about one or more artifacts, the pose is calculated based on the information, and the obtained image in step 610, described below, does not include the one or more artifacts. In some embodiments, the one or more poses may be determined based on a surgical plan or other preoperative imagery to take advantage of "windows" through bony structures (e.g., between adjacent vertebrae or portions thereof) in the anatomy in question. The one or more poses may be or include coordinates and/or an orientation of the imaging device. In some embodiments, the pose algorithm is configured to calculate the one or more poses based on the identified image information. For example, the one or more poses may be calculated based on an analysis of from which pose or positions and orientations the identified image information can be obtained. In other examples, the one or more poses may be calculated based on missing information (e.g., image data, anatomical feature properties) in a preoperative image or 3D model.

In some embodiments, the pose algorithm may be configured to calculate the one or more poses based on at least five degrees of freedom of movement of a robotic arm (e.g., the robotic arm 132) holding the imaging device. In other embodiments, the one or more poses may be based on less than or greater than five degrees of freedom of movement of the robotic arm. In some embodiments, the one or more poses is based on at least six degrees of freedom of movement of the robotic arm holding the imaging device. Such calculations based on multiple degrees of freedom of movement advantageously enables calculations of precise poses in planes and/or focal points that may not be obtainable by imaging devices without a robotic arm.

In other embodiments, the pose algorithm may be configured to calculate the one or more poses based on one or more characteristics of the imaging device (e.g., resolution, image type, image dimension, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more poses may be calculated that will ensure the area of interest is not in a "shadow" of the bony tissue. Also, in embodiments where the poses are calculated based at least in part on a preoperative image or 3D model of the surgical plan, the preoperative image or the 3D model may be utilized to enable calculation of poses that will enable needed information to be obtained in a more efficient manner than might otherwise be possible.

In some embodiments, the preoperative image or 3D model may comprise one or more artifacts, including but not limited to shadows caused by bony tissue as described above. The one or more poses may be calculated to obtain image data needed to update the preoperative image or 3D model and allow such artifacts to be eliminated from the preoperative image or 3D model, either entirely or in an area of interest.

In yet other embodiments, the pose algorithm may be configured to calculate the one or more poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method 600 further comprises determining at least one setting of the imaging device based on the pose and the plan (step 608). The at least one setting includes, but is not limited to, resolution, depth, type, and/or imaging duration. Determining the at least one setting may be based on at least one characteristic of the imaging device and/or the surgical plan. The at least one setting may also be based on the identified image information and/or the pose. For example, for a given image to be taken with an ultrasound probe at a certain pose, a long depth of penetration may be preferable to a high resolution, while for another image, the opposite may be true. In some embodiments, the at least one setting is based on input or feedback from the surgeon or operator. For example, the surgeon or operator may wish to obtain an image of an anatomical feature from a certain angle. The at least one setting may be different for each imaging device of a plurality of imaging devices that will be used to obtain the needed image information. In some embodiments, the at least one setting of one imaging device may be different for each image to be taken with the one imaging device, so as to obtain images with varying information. In other embodiments, the at least one setting may be determined during a calibration process.

The method further comprises receiving an image from the imaging device at the one or more poses using the determined at least one setting (step 610). In some embodiments, the image is received directly from the imaging device. In other embodiments, the image is received from or via a memory such as the memory 116, a database, the cloud or another network, or any other source or element. In some embodiments, the image is obtained prior to carrying out the surgical plan. In other embodiments, the image is obtained between two steps of the surgical plan. The identified image information may be extracted from the obtained image. The imaging device may be automatically positioned and/or automatically actuated to obtain the image. For example, the imaging device may be automatically positioned by a robotic arm such as the robotic arm 132 in the pose. In other examples, the imaging device may be positioned by a surgeon assisted by a navigation system such as the navigation system 114. The obtained image may comprise one or more 2D images, one or more 3D images, or a combination of one or more 2D images and one or more 3D images. Because each image is taken from a known location, the images can be readily combined, even if they are taken using different imaging devices.

In some embodiments, one imaging device may be used to obtain the image. In other embodiments, multiple imaging devices may be used to obtain the image. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In other embodiments, a first imaging device may obtain an image at each pose of a first set of the one or more poses and a second imaging device may obtain another image at each pose of a second set of the one or more poses.

Where only one pose is determined, one imaging device may be used to obtain one image at the one pose. Alternatively, one imaging device may be used to obtain a plurality of images at the one pose (perhaps, for example, with different settings for each image), or a plurality of imaging devices may be used to obtain a plurality of images at the one pose (e.g., to gather different types of image information from the one pose). In embodiments with multiple poses, one imaging device may be used to obtain one or more images at each of the multiple poses, or multiple imaging devices may be used. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In some embodiments, as previously described, the imaging device may be an ultrasound probe, and a detector or receiver of the ultrasound probe and an emitter or transducer of the ultrasound probe may be held a known distance from and opposite each other by separate robotic arms.

The method 600 may further comprise extracting the identified image information for the surgical plan from the obtained image. For example, information about an anatomical feature such as, but not limited to, veins may be extracted from the obtained image. In some embodiments, the method 600 may include updating an image or 3D object (e.g., of a surgical plan such as the surgical plan 134) based on each obtained image and based on the corresponding at least one pose to yield an updated image or 3D model.

The method 600 may further comprise calculating, based on the surgical plan, at least one predicted movement of an anatomical feature depicted in the image; determining an updated pose based on the predicted movement; determining at least one updated setting; causing the imaging device to obtain an updated image at the updated pose using the at least one updated setting; and verifying the predicted movement based on a comparison of the updated image and the corresponding image. The updated pose may match the pose calculated, for example, in step 606. The method 600 may further comprise identifying new information about the anatomical feature based on the update image. The surgical plan and/or a 3D model of the surgical plan may be updated based on the identified new information. The new information can be, but is not limited to, one or more of a change in a position and/or an orientation of the anatomical feature, a change in a surface characteristics of the anatomical feature, a change in a size of the anatomical feature, or an engagement of the anatomical feature with a surgical implant.

One or more of the steps 602-610 may be repeated when an anatomical feature has moved or is suspected to have moved. Repetition of the steps 602-610 may be performed and the surgical plan may be updated accordingly.

Figure 7:
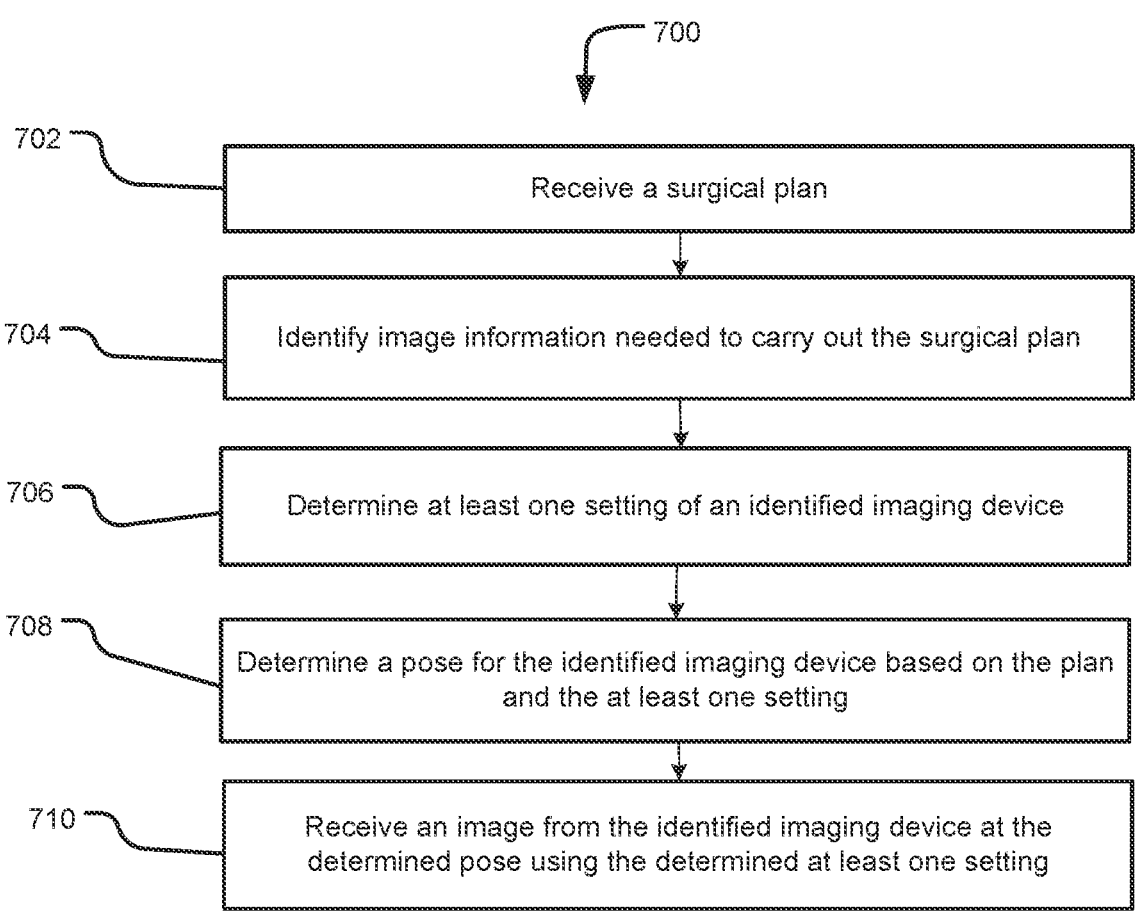
FIG. 7 is another flowchart of a method according to at least one embodiment of the present disclosure.

Turning now to FIG. 7, a method 700 for obtaining images based on a surgical plan such as the surgical plan 134 according to embodiments of the present disclosure may be executed, for example, in whole or in part, on a computing device such as the computing device 102 or a similar device, and may utilize one or more components of the system 100 or similar components. One or more aspects of the method 700 may be performed by or with a surgical robot, a surgeon, or a combination of both using one or more imaging devices such as the imaging device 112. Generally, method 700 is similar to method 600, except for steps 706 and 708 are different from steps 606 and 608.

The method 700 may be used, for example, to improve or optimize the settings of one or more imaging devices (such as, for example, an imaging device 112) prior to the use thereof to obtain one or more images, to increase the likelihood of obtaining useable images that have the desired information therein and to reduce the time needed to obtain such images. Currently, for example, a surgeon or other operator may need to take time to review a surgical plan, identify a needed image, determine which imaging device to use to obtain the needed image, review the settings of the imaging device, adjust those settings as necessary, take a trial image, re-adjust the settings to make any needed corrections, and then take one or more additional images. According to embodiments of the present disclosure, a processor (such as, for example, the processor 104) may analyze a surgical plan, identify information that needs to be gathered by obtaining one or more images of the relevant anatomical area, determine which of a plurality of imaging devices is best suited for obtaining the needed images, determine which settings of the selected imaging device(s) are needed to obtain the needed information, and then cause a robotic arm to automatically position the imaging device(s) in one or more appropriate positions and orientations to obtain the needed images—all with little or no input from a surgeon or other operator.

The method 700 may also be used, for example, to combine images from different imaging devices using the known positions and orientations of each imaging device. For example, images from an ultrasound device may be combined with images from an OCT camera based on the known positions and orientations of the ultrasound device and the OCT camera when each image is taken.

The method 700 may also be used, for example, for providing doppler imaging in which a first layer of image data may be portrayed on top of a second layer of image data. The first layer and the second layer may be different types of image data. For example, second layer of image data may be X-ray image data and the first layer of image data may be ultrasonic image data. In such examples, soft tissue (e.g., a flow of blood within a heart or vessels) may be displayed on top of hard tissue (e.g., bone). Such doppler imaging may be used to detect velocity changes of various elements. It will be appreciated that any number or type of image data layer may be portrayed on top of any number or type of image data.

The method 700 may also be used, for example, to eliminate artifacts from, or to reduce the number of artifacts in, a preoperative model or other imagery. A processor such as the processor 104 may be utilized to identify such artifacts (or to receive an input from a surgeon or other operator that identifies such artifacts), determine what additional information is needed to eliminate the artifacts from the preoperative model or other imagery, select one or more imaging devices to use to obtain the additional information, identify one or more needed settings of the selected imaging device, configure the imaging device to reflect the needed settings, calculate one or more poses at which to position the imaging device to obtain the needed images, and then cause the imaging device to obtain one or more images at the one or more poses (e.g., by controlling a robotic arm holding the imaging device to move the imaging device to the calculated pose, and by causing the imaging device to obtain an image once the imaging device has reached the calculated pose).

The method 700 comprises receiving a surgical plan (step 702). The surgical plan, which may be, for example, the same as or similar to the surgical plan 134, may be received via a user interface such as the user interface 110 and/or a communication interface such as the communication interface 108 of a computing device such as the computing device 102, and may be stored in a memory such as the memory 106 of the computing device. The surgical plan may also be generated by or uploaded to any component of the system 100. The surgical plan may include information about one or more planned movements of a robotic arm such as the robotic arm 132 to position an imaging device (e.g., the imaging device 112) during a surgical procedure. The information may also include a timeline or schedule of the one or more planned movements. The one or more planned movements may be or include one or more of timestamps, a type of movement (e.g., translational and/or rotational), a duration of the movement, and/or positional information (e.g., coordinates, orientation). The surgical plan may include information about one or more artifacts that may obscure or otherwise interfere with obtaining an image.

The surgical plan, in some embodiments, comprises a 3D model and/or other image data of a patient anatomy. In such embodiments, the image data may be processed using an image processing algorithm such as the imaging processing algorithm 120 to resolve gray level scales for calibrating an imaging device. During calibration, a normalized gray scale value may be applied to the imaging device.

The method 700 also comprises identifying image information needed to carry out the surgical plan (step 704). The needed image information may be or include information about one or more anatomical features (including, for example, location (including location relative to one or more other anatomical features), properties and/or types of the one or more anatomical features), and/or required image depth, resolution, and/or type.

The method 700 may also comprise identifying an imaging device needed to obtain the identified image information. The imaging device (which may be, for example, an imaging device 112) may be selected based on the needed image information. For example, the imaging device may be selected based on whether characteristics of the imaging device enable the imaging device to obtain the identified image information. For example, one imaging device (e.g., an OCT camera) may be selected based on a need for detailed images of anatomical features near a surface of the anatomical tissue, and/or because imaging over a long period of time is needed (such that X-ray radiation and/or ultrasonic heating would be a concern if an X-ray imaging device or ultrasonic imaging device, respectively, were used). Another imaging device (e.g., an ultrasound probe) may be selected based on a need for images at a greater depth. The imaging device may also be selected based on dimensions of the imaging device. For example, an imaging device may be selected for its ability to fit through a small incision and/or to be used in a minimally invasive surgical system. In some embodiments, two or more imaging devices (or one imaging device with two or more configurations) may be needed to gather all of the identified imaging information. For example, an ultrasound probe may be used to gather imaging information at greater depths, and an OCT device may be used to gather imaging information at shallower depths. In other embodiments, an OCT device may be used for internal imaging (e.g., of an artery) while an ultrasound probe is used for external imaging.

The method 700 further comprises determining at least one setting of the imaging device (step 706). Determining the at least one setting may be based on the surgical plan. The at least one setting includes, but is not limited to, resolution, depth, type, and/or imaging duration. Determining the at least one setting may be based on at least one characteristic of the imaging device and/or the surgical plan. The at least one setting may also be based on the identified image information and/or the pose. For example, for a given image to be taken with an ultrasound probe at a certain pose, a long depth of penetration may be preferable to a high resolution, while for another image, the opposite may be true. In some embodiments, the at least one setting is based on input or feedback from the surgeon or operator. For example, the surgeon or operator may wish to obtain an image of an anatomical feature from a certain angle. The at least one setting may be different for each imaging device of a plurality of imaging devices that will be used to obtain the needed image information. In some embodiments, the at least one setting of one imaging device may be different for each image to be taken with the one imaging device, so as to obtain images with varying information. In other embodiments, the at least one setting may be determined during a calibration process.

The method 700 also comprises determining a pose for the imaging device based on the plan and the at least one setting (step 708). The one or more poses may be determined using a pose algorithm such as the pose algorithm 122. The one or more poses may be determined based at least in part on the surgical plan and/or other information about the anatomy to be imaged, so as to determine poses of the imaging device that will provide as much information as possible. This is particularly important, for example, when imaging complex bony structures, such as the spinal vertebrae, which (depending on the imaging device used) may create shadows and thus reduce the amount of information that can be gathered from an image. In embodiments where the surgical plan includes a 3D model, determining the pose may be further based on the 3D model. In such embodiments, the 3D model includes information about one or more artifacts, the pose is calculated based on the information, and the obtained image in step 710, described below, does not include the one or more artifacts. In some embodiments, the one or more poses may be determined based on a surgical plan or other preoperative imagery to take advantage of "windows" through bony structures (e.g., between adjacent vertebrae or portions thereof) in the anatomy in question. The one or more poses may be or include coordinates and/or an orientation of the imaging device. In some embodiments, the pose algorithm is configured to calculate the one or more poses based on the identified image information. For example, the one or more poses may be calculated based on an analysis of from which pose or positions and orientations the identified image information can be obtained. In other examples, the one or more poses may be calculated based on missing information (e.g., image data, anatomical feature properties) in a preoperative image or 3D model.

In some embodiments, the pose algorithm may be configured to calculate the one or more poses based on at least five degrees of freedom of movement of a robotic arm (e.g., the robotic arm 132) holding the imaging device. In other embodiments, the one or more poses may be based on less than or greater than five degrees of freedom of movement of the robotic arm. In some embodiments, the one or more poses is based on at least six degrees of freedom of movement of the robotic arm holding the imaging device. Such calculations based on multiple degrees of freedom of movement advantageously enables calculations of precise poses in planes and/or focal points that may not be obtainable by imaging devices without a robotic arm.

In other embodiments, the pose algorithm may be configured to calculate the one or more poses based on one or more characteristics of the imaging device (e.g., resolution, image type, image dimension, device dimensions, image depth, etc.). For example, if the area to be imaged includes bony tissue, and the imaging device is an ultrasound probe, then the one or more poses may be calculated to avoid "shadows" caused by the inability of ultrasound waves to penetrate the bony tissue. More specifically, the one or more poses may be selected, for example, to obtain image data from two different trajectories on different sides of the bony tissue, so that portions of the imaged area that are in a "shadow" in one image are clearly shown in the other, and vice versa. Alternatively, if information is needed only about the anatomy on one side of the bony tissue, one or more poses may be calculated that will ensure the area of interest is not in a "shadow" of the bony tissue. Also, in embodiments where the poses are calculated based at least in part on a preoperative image or 3D model of the surgical plan, the preoperative image or the 3D model may be utilized to enable calculation of poses that will enable needed information to be obtained in a more efficient manner than might otherwise be possible.

In some embodiments, the preoperative image or 3D model may comprise one or more artifacts, including but not limited to shadows caused by bony tissue as described above. The one or more poses may be calculated to obtain image data needed to update the preoperative image or 3D model and allow such artifacts to be eliminated from the preoperative image or 3D model, either entirely or in an area of interest.

In yet other embodiments, the pose algorithm may be configured to calculate the one or more poses based on input or feedback from the surgeon or operator. For example, the surgeon or operator may wish to obtain an image of an anatomical feature from a certain angle or plurality of angles. In another example, the surgeon may wish to non-invasively position the imaging device, while in other examples the surgeon may wish to invasively position the imaging device.

The method further comprises receiving an image from the identified imaging device an image at the one or more poses using the determined at least one setting (step 710). In some embodiments, the image is received directly from the imaging device. In other embodiments, the image is received from or via a memory such as the memory 116, a database, the cloud or another network, or any other source or element. In some embodiments, the image is obtained prior to carrying out the surgical plan. In other embodiments, the image is obtained between two steps of the surgical plan. The identified image information may be extracted from the obtained image. The imaging device may be automatically positioned and/or automatically actuated to obtain the image. For example, the imaging device may be automatically positioned by a robotic arm such as the robotic arm 132 in the pose. In other examples, the imaging device may be positioned by a surgeon assisted by a navigation system such as the navigation system 114. The obtained image may comprise one or more 2D images, one or more 3D images, or a combination of one or more 2D images and one or more 3D images. Because each image is taken from a known location, the images can be readily combined, even if they are taken using different imaging devices.

In some embodiments, one imaging device may be used to obtain the image. In other embodiments, multiple imaging devices may be used to obtain the image. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In other embodiments, a first imaging device may obtain an image at each pose of a first set of the one or more poses and a second imaging device may obtain another image at each pose of a second set of the one or more poses.

Where only one pose is determined, one imaging device may be used to obtain one image at the one pose. Alternatively, one imaging device may be used to obtain a plurality of images at the one pose (perhaps, for example, with different settings for each image), or a plurality of imaging devices may be used to obtain a plurality of images at the one pose (e.g., to gather different types of image information from the one pose). In embodiments with multiple poses, one imaging device may be used to obtain one or more images at each of the multiple poses, or multiple imaging devices may be used. For example, a first imaging device may obtain a first one of the images independently of a second imaging device obtaining a second one of the images. In another example, at least a first one of the images may be obtained with a first imaging device held by a robotic arm in a corresponding first one of the poses and at least a second one of the images may be obtained with a second imaging device held by the robotic arm in a corresponding second one of the poses. In some embodiments, as previously described, the imaging device may be an ultrasound probe, and a detector or receiver of the ultrasound probe and an emitter or transducer of the ultrasound probe may be held a known distance from and opposite each other by separate robotic arms.

The method 700 may further comprise extracting the identified image information for the surgical plan from the obtain image. For example, information about an anatomical feature such as, but not limited to, veins may be extracted from the obtained image. In some embodiments, the method 700 may include updating an image or 3D object (e.g., of a surgical plan such as the surgical plan 134) based on each obtained image and based on the corresponding at least one pose to yield an updated image or 3D model.

The method 700 may further comprise calculating, based on the surgical plan, at least one predicted movement of an anatomical feature depicted in the image; determining an updated pose based on the predicted movement; determining at least one updated setting; causing the imaging device to obtain an updated image at the updated pose using the at least one updated setting; and verifying the predicted movement based on a comparison of the updated image and the corresponding image. The updated pose may match the pose calculated, for example, in step 707. The method 700 may further comprise identifying new information about the anatomical feature based on the update image. The surgical plan and/or a 3D model of the surgical plan may be updated based on the identified new information.

One or more of the steps 702-710 may be repeated when an anatomical feature has moved or is suspected to have moved. Repetition of the steps 702-710 may be performed and the surgical plan may be updated accordingly.

Figure 8:
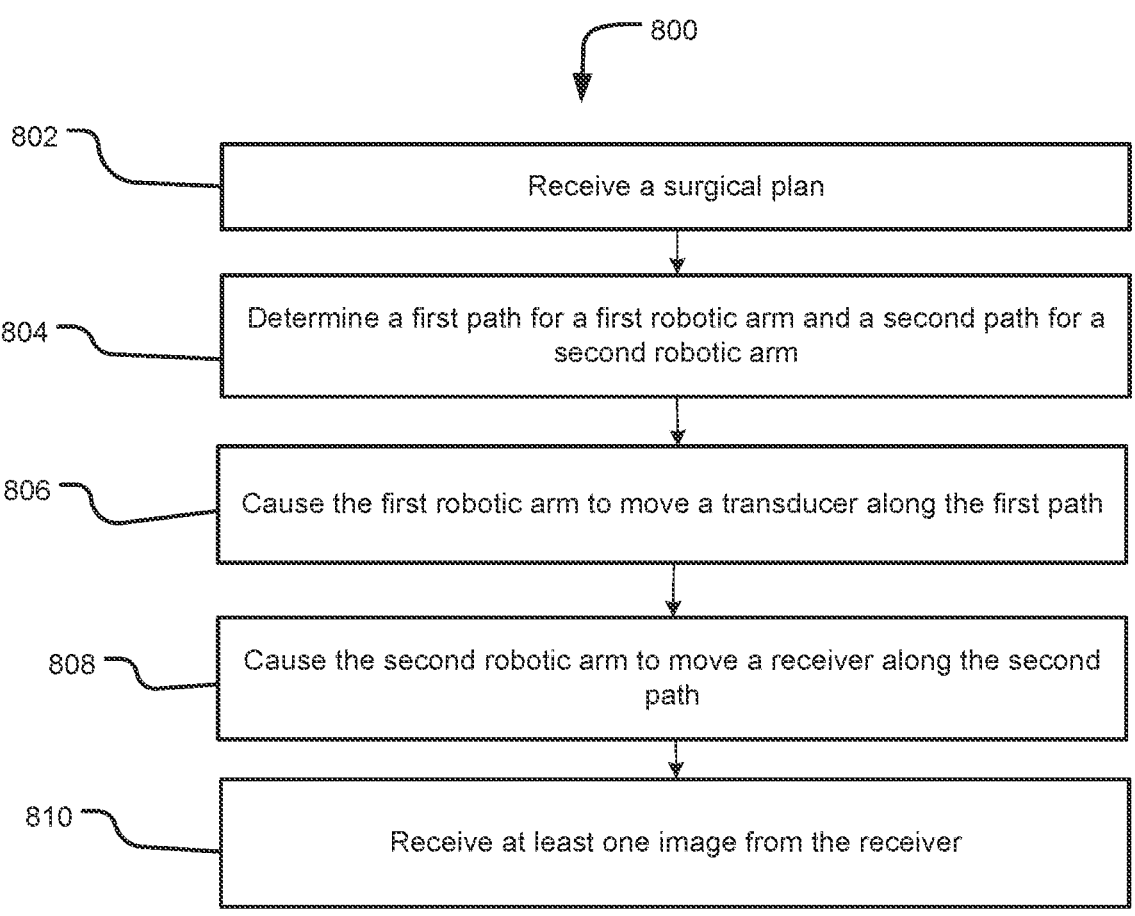
FIG. 8 is another flowchart of a method according to at least one embodiment of the present disclosure.

Turning now to FIG. 8, a method 800 for obtaining time of flight images based on a surgical plan such as the surgical plan 134 according to embodiments of the present disclosure may be executed, for example, in whole or in part, on a computing device such as the computing device 102 or a similar device, and may utilize one or more components of the system 100 or similar components. One or more aspects of the method 800 may be performed by or with a surgical robot, a surgeon, or a combination of both using one or more imaging devices such as the imaging device 112. The method 800 may be used, for example, to provide information about tissue unique to time of flight images.

The method 800 comprises receiving a surgical plan (step 802). The surgical plan, which may be, for example, the same as or similar to the surgical plan 134, may be received via a user interface such as the user interface 110 and/or a communication interface such as the communication interface 108 of a computing device such as the computing device 102, and may be stored in a memory such as the memory 106 of the computing device. The surgical plan may also be generated by or uploaded to any component of the system 100. The surgical plan may include information about one or more planned movements of a robotic arm such as the robotic arm 132 to position an imaging device (e.g., the imaging device 112) during a surgical procedure. The surgical plan, in some embodiments, includes information about a region of interest of a patient, such as an initial image of the region of interest and/or other image data of a patient anatomy. The initial image may be, in some embodiments, a registered pre-acquired scan. The surgical plan may include information about a first pose or path for a first robotic arm, a second pose or path for a second robotic arm, and/or a third pose or path for a third robotic arm. The surgical plan can include any number of paths or poses for any number of robotic arms. In other embodiments, the surgical plan does not include any paths or poses and such paths or poses may be determined as described below with respect to step 804.

The surgical plan may include information about one or more planned movements of one or more robotic arm such as the robotic arm 132 to position an imaging device (e.g., the imaging device 112, which may comprise a transducer and a receiver physically separate from the transducer) during a surgical procedure. The information may also include a timeline or schedule of the one or more planned movements. The one or more planned movements may be or include one or more of timestamps, a type of movement (e.g., translational and/or rotational), a duration of the movement, and/or positional information (e.g., coordinates, orientation).

The method 800 also comprises determining a first path for a first robotic arm and a second path for a second robotic arm (step 804). The determining step may be based on the surgical plan including, but not limited to, information about a region of interest of a patient anatomy, such as the initial image. The determining may additionally or alternatively be based on a real-time optical scan. The determining may use one or more algorithms such as the pose algorithm 122. The first path and the second path may each include a plurality of coordinates and/or orientations for a transducer held by the first robotic arm and for a receiver held by the second robotic arm, respectively. In some embodiments, the determining step determines a third path for a third robotic arm. In other embodiments, the determining step may determine any number of paths for any number of robotic arms.

In some embodiments, determining the first path comprises determining a plurality of first poses defining the first path, and determining the second path comprises determining a plurality of second poses defining the second path. In such embodiments, determining each of the first poses each of the second poses may be based on the information about the region of interest of the patient anatomy, such as the initial image. For example, the first path and the second path may each be determined based on obtaining a three-dimensional image of a particular organ. Each of the first path and the second path may be at least one of or a combination of intra-corporeal or extra-corporeal paths. Further, each of the first path and the second path can be at least one of or a combination of circular, parallel, or free-shaped.

The method 800 comprises causing the first robotic arm to move on the first path (step 806) and causing the second robotic arm to move on the second path (step 808). In some embodiments, including when a three-dimensional image is desired, the first robotic arm moves on the first path synchronously to the second robotic arm moving on the second path. In other embodiments, including when a two-dimensional image is desired, the first robotic arm does not move synchronously to the second robotic arm, although the two robotic arms do maintain the transducer and the receiver directly or substantially facing each other so as to ensure that signals emitted by the transducer are received by the receiver.

In some embodiments, the first robotic arm is configured to hold a transducer and the second robotic arm is configured to hold a receiver. In other embodiments, the transducer is a first transducer and the method 800 further comprises causing the third robotic arm to move on the third path. In the same embodiments, the third robotic arm is configured to hold a second transducer and the second transducer has an image setting different from the first transducer. In some embodiments, the image setting may be at least one of a frequency and/or an amplitude.

The method 800 also comprises receiving at least one image from the receiver (step 810). The at least one image is generated based on time of flight measurements obtained during movement of the first robotic arm on the first path, the second robotic arm on the second path, and (where utilized) the third robotic arm on the third path. Such measurements may be based at least in part on a known pose of the transducer(s) and receiver, respectively, at the moment each signal was sent and received. The image may depict patient anatomy. In embodiments where the transducer includes more than two transducers, the image may be an elastographic image. In some embodiments, a three-dimensional model may be reconstructed from the at least one image.

In some embodiments, the method 800 further comprises determining a frequency to be used by the imaging device (e.g., by the transducer when generating ultrasonic signals). The frequency may be determined based on, for example, a known tissue composition of the region of interest. In some embodiments, the determined frequency may be presented to a user (e.g., via a user interface) as a recommended frequency, which the user can accept or reject. In other embodiments, the determined frequency may be used to automatically configure the imaging device. In still other embodiments, the method 800 may comprise receiving (e.g., via a user interface) a frequency selection from a user.

The method 800 may also comprise, in some embodiments, calculating a pressure amplitude required to achieve the needed penetration of the tissue positioned between the transducer and the receiver of the imaging device. The calculating may be based on, for example, the determined frequency.

The methods and systems described herein provide improved imaging methods using known positions and orientations of the images for updating, registering, or generating an initial image or model. The methods and systems also provide for improved updating or re-registration of the initial image or model throughout the operation as the known positions and orientations of the original images or model provides for recreation of the images from the exact positions and orientations as the original images or model.

As may be appreciated based on the foregoing disclosure, the present disclosure encompasses methods with fewer than all of the steps identified in FIGS. 2, 3, 4, 5, 6, 7 and 8 (and the corresponding description of the methods 200, 300, 400, 500, 600, 700 and 800), as well as methods that include additional steps beyond those identified in FIGS. 2, 3, 4, 5, 6, 7 and 8 (and the corresponding description of the methods 200, 300, 400, 500, 600, 700 and 800).

The foregoing discussion has been presented for purposes of illustration and description. The foregoing is not intended to limit the disclosure to the form or forms disclosed herein. In the foregoing Detailed Description, for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method comprising:
   receiving a surgical plan, the surgical plan having at least one preoperative image;
   determining, based on the surgical plan, a first path for a first robotic arm, a second path for a second robotic arm, and a third path for a third robotic arm;
   causing the first robotic arm to move on the first path, the first robotic arm configured to hold a first transducer configured to emit sound waves;
   causing the second robotic arm to move on the second path, the second robotic arm configured to hold a receiver configured to detect the sound waves;
   causing the third robotic arm to move on the third path, the third robotic arm configured to hold a second transducer that has at least one image setting different from the first transducer;
   calculating, based on a patient anatomy to be imaged, a pressure amplitude for the sound waves to achieve penetration through the patient anatomy from the first transducer and the second transducer to the receiver;
   configuring at least one of the first transducer, the second transducer, and the receiver with the pressure amplitude;
   receiving at least one first image from the receiver captured during a first time period, the at least one first image depicting the patient anatomy and generated using first time-of-flight measurements that correspond to first amounts of time taken for first sound waves to travel through the patient anatomy from the first transducer to the receiver and to second amounts of time taken for second sound waves to travel through the patient anatomy from the second transducer to the receiver;
   registering a robotic space to a patient space based on the at least one first image and the at least one preoperative image;
   receiving at least one second image from the receiver captured during a second time period, the at least one second image depicting the patient anatomy and generated using second time-of-flight measurements that correspond to third amounts of time taken for third sound waves to travel through the patient anatomy from the first transducer to the receiver and to fourth amounts of time taken for fourth sound waves to travel through the patient anatomy from the second transducer to the receiver; and
   comparing the at least one first image to the at least one second image to verify the registration.

2. The method of claim 1, wherein poses of the first robotic arm moving on the first path, poses of the second robotic arm moving on the second path, and poses of the third robotic arm moving on the third path are such that spaces between the first transducer and the receiver and between the second transducer and the receiver are substantially air-free.

3. The method of claim 1, wherein the first robotic arm moves on the first path on a first side of the patient anatomy while the second robotic arm moves synchronously along the second path on a second side of the patient anatomy opposite the first side.

4. The method of claim 1, wherein comparing the at least one first image to the at least one second image to verify the registration comprises:
   determining a position of an anatomical feature in the at least one first image and a position of the anatomical feature in the at least one second image;
   verifying the registration when the position of the anatomical feature in the at least one first image matches the position of the anatomical feature in the at least one second image, and wherein the method further comprises:
   reregistering the robotic space to the patient space based on the at least one second image and the at least one preoperative image when the position of the anatomical feature in the at least one first image does not match the position of the anatomical feature in the at least one second image.

5. The method of claim 1, wherein the surgical plan includes information about a region of interest of the patient anatomy, and wherein determining the first path, the second path, and the third path is based on the information.

6. The method of claim 1, wherein the image setting is at least one of a frequency and/or an amplitude.

7. The method of claim 1, wherein the at least one first image and the at least one second image each comprise an elastography image.

8. The method of claim 1, wherein each of the first path, the second path, and the third path is at least one of or a combination of an intra-corporeal path or an extra-corporeal path.

9. The method of claim 1, wherein each of the first path, the second path, and the third path is at least one of or a combination of circular, parallel, or free-shaped.

10. A device comprising:
   at least one processor; and
   at least one memory storing instructions for execution by the at least one processor that, when executed, cause the at least one processor to:
   receive a surgical plan, the surgical plan having at least one preoperative image;
   determine, based on the surgical plan, a first path for a first robotic arm, a second path for a second robotic arm, and a third path for a third robotic arm;
   cause the first robotic arm to move on the first path, the first robotic arm holding a first transducer configured to emit sound waves;
   cause the second robotic arm to move on the second path, the second robotic arm holding a receiver configured to detect the sound waves;
   cause the third robotic arm to move on the third path, the third robotic arm holding a second transducer that has at least one image setting different from the first transducer;
   calculate, based on a patient anatomy to be imaged, a pressure amplitude for the sound waves to achieve penetration through the patient anatomy from the first transducer and the second transducer to the receiver;

configure at least one of the first transducer, the second transducer, and the receiver with the pressure amplitude;

receive at least one first image from the receiver captured during a first time period, the at least one first image depicting the patient anatomy and generated using first time-of-flight measurements that correspond to first amounts of time taken for first sound waves to travel through the patient anatomy from the first transducer to the receiver and to second amounts of time taken for second sound waves to travel through the patient anatomy from the second transducer to the receiver;

register a robotic space to a patient space based on the at least one first image and the at least one preoperative image;

receive at least one second image from the receiver captured during a second time period, the at least one second image depicting the patient anatomy and generated using second time-of-flight measurements that correspond to third amounts of time taken for third sound waves to travel through the patient anatomy from the first transducer to the receiver and to fourth amounts of time taken for fourth sound waves to travel through the patient anatomy from the second transducer to the receiver; and compare the at least one first image to the at least one second image to verify the registration.

11. The device of claim 10, wherein poses of the first robotic arm moving on the first path, and poses of the second robotic arm moving on the second path, and poses of the third robotic arm moving along the third path are such that spaces between the first transducer and the receiver and between the second transducer and the receiver are substantially air-free.

12. The device of claim 10, wherein the first robotic arm moves on the first path on a first side of the patient anatomy while the second robotic arm moves synchronously along the second path on a second side of the patient anatomy opposite the first side.

13. The device of claim 10, wherein the at least one first image is a three-dimensional model.

14. The device of claim 10, wherein the surgical plan includes information about a region of interest of the patient anatomy, and wherein determining the first path, the second path, and the third path is based on the information.

15. The device of claim 10, wherein the image setting is at least one of a frequency and/or an amplitude.

16. The device of claim 10, wherein the at least one first image and the at least one second image each comprise an elastographic image.

17. The device of claim 10, wherein each of the first path, the second path, and the third path is at least one of or a combination of an intra-corporeal path or an extra-corporeal path.

18. A system comprising:

an imaging device comprising a first transducer configured to emit sound waves, a second transducer configured to emit sound waves and having at least one image setting different than the first transducer, and a receiver configured to detect the sound waves;

a plurality of robotic arms, a first robotic arm of the plurality of robotic arms configured to hold the first transducer, a second robotic arm of the plurality of robotic arms configured to hold the receiver, and a third robotic arm of the plurality of robotic arms configured to hold the second transducer;

at least one processor; and at least one memory storing instructions for execution by the at least one processor that, when executed, cause the at least one processor to:

receive a surgical plan, the surgical plan having at least one preoperative image;

determine, based on the surgical plan, a first path for the first robotic arm, a second path for the second robotic arm, and a third path for the third robotic arm;

cause the first robotic arm to move on the first path, the first robotic arm holding the first transducer;

cause the second robotic arm to move on the second path, the second robotic arm holding the receiver;

cause the third robotic arm to move on the third path, the third robotic arm holding the second transducer;

calculate, based on a patient anatomy to be imaged, a pressure amplitude for the sound waves to achieve penetration through the patient anatomy from the first transducer and second transducer to the receiver;

configure at least one of the first transducer, the second transducer, and the receiver with the pressure amplitude;

receive at least one first image from the receiver captured duringat a time period, the at least one first image depicting the patient anatomy and generated using first time-of-flight measurements that correspond to first amounts of time taken for first sound waves to travel through the patient anatomy from the first transducer to the receiver and to second amounts of time taken for second sound waves to travel through the patient anatomy from the second transducer to the receiver;

register a robotic space to a patient space based on the at least one first image and the at least one preoperative image;

receive at least one second image from the receiver captured during a second time period, the at least one second image depicting the patient anatomy and generated using second time-of-flight measurements that correspond to third amounts of time taken for third sound waves to travel through the patient anatomy from the first transducer to the receiver and to fourth amounts of time taken for fourth sound waves to travel through the patient anatomy from the second transducer to the receiver; and compare the at least one first image to the at least one second image to verify the registration.

* * * * *